(12) United States Patent
Chomas et al.

(10) Patent No.: US 9,808,332 B2
(45) Date of Patent: *Nov. 7, 2017

(54) DYNAMIC MICROVALVE PROTECTION DEVICE

(71) Applicant: Surefire Medical, Inc., Westminster, CO (US)

(72) Inventors: James E. Chomas, Denver, CO (US); Leonard Pinchuk, Miami, FL (US); John Martin, Miami, FL (US); Aravind Arepally, Atlanta, GA (US); Brett E. Naglreiter, Hollywood, FL (US); Bryan M. Pinchuk, Miami, FL (US)

(73) Assignee: Surefire Medical, Inc., Westminster, CO (US)

( * ) Notice: Subject to any disclaimer, the term of this patent is extended or adjusted under 35 U.S.C. 154(b) by 287 days.

This patent is subject to a terminal disclaimer.

(21) Appl. No.: 14/806,596

(22) Filed: Jul. 22, 2015

(65) Prior Publication Data

US 2016/0015508 A1    Jan. 21, 2016

Related U.S. Application Data

(63) Continuation of application No. 13/306,105, filed on Nov. 29, 2011, now Pat. No. 9,539,081, which is a
(Continued)

(51) Int. Cl.
*A61M 29/00*    (2006.01)
*A61F 2/06*    (2013.01)
(Continued)

(52) U.S. Cl.
CPC ........ *A61F 2/013* (2013.01); *A61B 17/12186* (2013.01); *A61F 2/01* (2013.01);
(Continued)

(58) Field of Classification Search
CPC ........... A61M 25/0075; A61M 25/0076; A61F 2/013; A61F 2/2412; A61F 2/2436; A61B 17/12186
See application file for complete search history.

(56) References Cited

U.S. PATENT DOCUMENTS

| 4,738,740 | A | 4/1988 | Pinchuk et al. |
| 5,234,425 | A | 8/1993 | Fogarty et al. |

(Continued)

FOREIGN PATENT DOCUMENTS

| EP | 1226795 | 7/2002 |
| EP | 1803423 | 7/2007 |

(Continued)

OTHER PUBLICATIONS

US 7,169,126, 01/2007, Zadno-Azizi (withdrawn)
(Continued)

*Primary Examiner* — Kathleen Holwerda
*Assistant Examiner* — Lindsey Bachman
(74) *Attorney, Agent, or Firm* — Gordon & Jacobson, P.C.

(57) ABSTRACT

An apparatus includes a delivery catheter having a deployable dynamic valve that dynamically opens and closes in response to relative fluid pressure thereabout, particularly while in an anatomical lumen. The valve is maintained in a collapsed configuration during introduction to a treatment site. The valve is adapted to automatically move from the collapsed configuration to a deployed configuration at the treatment site.

19 Claims, 28 Drawing Sheets

Related U.S. Application Data continuation-in-part of application No. 12/957,533, filed on Dec. 1, 2010, now Pat. No. 8,696,698, which is a continuation-in-part of application No. 12/829,565, filed on Jul. 2, 2010, now Pat. No. 8,500,775.

(60) Provisional application No. 61/382,290, filed on Sep. 13, 2010, provisional application No. 61/266,068, filed on Dec. 2, 2009.

(51) Int. Cl.

| | | |
|---|---|---|
| *A61F 2/01* | (2006.01) | |
| *A61B 17/12* | (2006.01) | |
| *A61F 2/24* | (2006.01) | |
| *A61B 17/00* | (2006.01) | |
| *A61B 17/22* | (2006.01) | |
| *A61M 25/00* | (2006.01) | |

(52) U.S. Cl.
CPC .......... *A61F 2/2412* (2013.01); *A61F 2/2436* (2013.01); *A61M 25/0075* (2013.01); *A61B 17/00491* (2013.01); *A61B 2017/22082* (2013.01); *A61F 2002/011* (2013.01); *A61F 2002/016* (2013.01); *A61F 2002/018* (2013.01); *A61F 2230/0006* (2013.01); *A61F 2230/008* (2013.01); *A61F 2230/0067* (2013.01); *A61F 2230/0076* (2013.01); *A61M 25/005* (2013.01); *A61M 2025/0004* (2013.01)

(56) References Cited

U.S. PATENT DOCUMENTS

| | | |
|---|---|---|
| 5,893,869 A | 4/1999 | Barnhart et al. |
| 5,895,399 A | 4/1999 | Barbut et al. |
| 5,910,154 A | 6/1999 | Tsugita et al. |
| 5,911,734 A | 6/1999 | Tsugita et al. |
| 6,001,118 A | 12/1999 | Daniel et al. |
| 6,010,522 A | 1/2000 | Barbut et al. |
| 6,027,520 A | 2/2000 | Tsugita et al. |
| 6,042,598 A | 3/2000 | Tsugita et al. |
| 6,059,745 A | 5/2000 | Gelbfish |
| 6,152,946 A | 11/2000 | Broome et al. |
| 6,165,200 A | 12/2000 | Tsugita et al. |
| 6,168,579 B1 | 1/2001 | Tsugita |
| 6,179,851 B1 | 1/2001 | Barbut et al. |
| 6,235,044 B1 | 5/2001 | Root et al. |
| 6,258,120 B1 | 7/2001 | McKenzie et al. |
| 6,306,074 B1 | 10/2001 | Waksman et al. |
| 6,306,163 B1 | 10/2001 | Fitz |
| 6,309,399 B1 | 10/2001 | Barbut et al. |
| 6,361,545 B1 | 3/2002 | Macoviak et al. |
| 6,371,969 B1 | 4/2002 | Tsugita et al. |
| 6,371,971 B1 | 4/2002 | Tsugita et al. |
| 6,383,206 B1 | 5/2002 | Gillick et al. |
| 6,395,014 B1 | 5/2002 | Macoviak et al. |
| 6,436,112 B2 | 8/2002 | Wensel et al. |
| 6,443,926 B1 | 9/2002 | Kletschka |
| 6,485,456 B1 | 11/2002 | Kletschka |
| 6,485,502 B2 | 11/2002 | Don Michael et al. |
| 6,499,487 B1 | 12/2002 | McKenzie et al. |
| 6,530,935 B2 | 3/2003 | Wensel et al. |
| 6,533,800 B1 | 3/2003 | Barbut |
| 6,537,294 B1 | 3/2003 | Boyle et al. |
| 6,537,297 B2 | 3/2003 | Tsugita et al. |
| 6,540,722 B1 | 4/2003 | Boyle et al. |
| 6,551,303 B1 | 4/2003 | Van Tassel et al. |
| 6,582,396 B1 | 6/2003 | Parodi |
| 6,589,264 B1 | 7/2003 | Barbut et al. |
| 6,592,546 B1 | 7/2003 | Barbut et al. |
| 6,607,506 B2 | 8/2003 | Kletschka |
| 6,620,148 B1 | 9/2003 | Tsugita |
| 6,635,070 B2 | 10/2003 | Leeflang et al. |
| 6,645,220 B1 | 11/2003 | Huter et al. |
| 6,645,222 B1 | 11/2003 | Parodi et al. |
| 6,645,223 B2 | 11/2003 | Boyle et al. |
| 6,652,555 B1 | 11/2003 | VanTassel et al. |
| 6,652,556 B1 | 11/2003 | VanTassel et al. |
| 6,656,351 B2 | 12/2003 | Boyle |
| 6,673,090 B2 | 1/2004 | Root et al. |
| 6,676,682 B1 | 1/2004 | Tsugita et al. |
| 6,689,150 B1 | 2/2004 | VanTassel et al. |
| 6,692,508 B2 | 2/2004 | Wensel et al. |
| 6,692,509 B2 | 2/2004 | Wensel et al. |
| 6,692,513 B2 * | 2/2004 | Streeter .................. A61F 2/01 606/200 |
| 6,695,813 B1 | 2/2004 | Boyle et al. |
| 6,695,858 B1 | 2/2004 | Dubrul et al. |
| 6,702,834 B1 | 3/2004 | Boylan et al. |
| 6,706,053 B1 | 3/2004 | Boylan et al. |
| 6,706,055 B2 | 3/2004 | Douk et al. |
| 6,730,108 B2 | 5/2004 | VanTassel et al. |
| 6,746,469 B2 | 6/2004 | Mouw |
| 6,818,006 B2 | 11/2004 | Douk et al. |
| 6,830,579 B2 | 12/2004 | Barbut |
| 6,837,898 B2 | 1/2005 | Boyle et al. |
| 6,855,154 B2 | 2/2005 | Abdel-Gawwad |
| 6,866,677 B2 | 3/2005 | Douk et al. |
| 6,887,258 B2 | 5/2005 | Denison et al. |
| 6,896,690 B1 * | 5/2005 | Lambrecht ............ A61F 2/2427 604/96.01 |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,936,060 B2 | 8/2005 | Hogendijk et al. |
| 6,939,362 B2 | 9/2005 | Boyle et al. |
| 6,964,670 B1 | 11/2005 | Shah et al. |
| 6,964,673 B2 | 11/2005 | Tsugita et al. |
| 6,974,469 B2 | 12/2005 | Broome et al. |
| 6,989,027 B2 * | 1/2006 | Allen .................... A61F 2/2412 606/200 |
| 7,044,958 B2 | 5/2006 | Douk et al. |
| 7,044,966 B2 | 5/2006 | Svanidze et al. |
| 7,066,946 B2 | 6/2006 | Douk et al. |
| 7,101,396 B2 | 9/2006 | Artof et al. |
| 7,162,303 B2 | 1/2007 | Levin et al. |
| 7,169,164 B2 | 1/2007 | Borillo et al. |
| 7,172,614 B2 | 2/2007 | Boyle et al. |
| 7,172,621 B2 | 2/2007 | Theron |
| 7,214,237 B2 | 5/2007 | Don Michael et al. |
| 7,217,255 B2 | 5/2007 | Boyle et al. |
| 7,223,253 B2 | 5/2007 | Hogendijk |
| 7,232,452 B2 | 6/2007 | Adams et al. |
| 7,232,453 B2 | 6/2007 | Shimon |
| 7,241,304 B2 | 7/2007 | Boyle et al. |
| 7,250,041 B2 | 7/2007 | Chiu et al. |
| 7,252,675 B2 | 8/2007 | Denison et al. |
| 7,279,000 B2 | 10/2007 | Cartier et al. |
| 7,306,575 B2 | 12/2007 | Barbut et al. |
| 7,322,957 B2 | 1/2008 | Kletschka et al. |
| 7,326,226 B2 | 2/2008 | Root et al. |
| 7,331,973 B2 | 2/2008 | Gesswein et al. |
| 7,338,510 B2 | 3/2008 | Boylan et al. |
| 7,344,549 B2 | 3/2008 | Boyle et al. |
| 7,371,249 B2 | 5/2008 | Douk et al. |
| 7,425,215 B2 | 9/2008 | Boyle et al. |
| 7,537,600 B2 | 5/2009 | Eskuri |
| 7,544,202 B2 | 6/2009 | Cartier et al. |
| 7,572,272 B2 | 8/2009 | Denison et al. |
| 7,582,100 B2 | 9/2009 | Johnson et al. |
| 7,585,309 B2 | 9/2009 | Larson |
| 7,591,832 B2 | 9/2009 | Eversull et al. |
| 7,604,650 B2 | 10/2009 | Bergheim |
| 7,647,115 B2 | 1/2010 | Levin et al. |
| 7,653,438 B2 | 1/2010 | Deem et al. |
| 7,833,242 B2 | 11/2010 | Gilson et al. |
| 7,842,084 B2 | 11/2010 | Bicer |
| 7,853,333 B2 | 12/2010 | Demarais |
| 7,873,417 B2 | 1/2011 | Demarais et al. |
| 7,937,143 B2 | 5/2011 | Demarais et al. |
| 8,500,775 B2 | 8/2013 | Chomas et al. |
| 8,696,698 B2 | 4/2014 | Chomas et al. |
| 8,696,699 B2 | 4/2014 | Chomas et al. |

(56) References Cited

U.S. PATENT DOCUMENTS

| | | |
|---|---|---|
| 9,089,341 B2 | 7/2015 | Chomas et al. |
| 2002/0161390 A1 | 10/2002 | Mouw |
| 2002/0161394 A1 | 10/2002 | Macoviak et al. |
| 2003/0187474 A1 | 10/2003 | Keegan et al. |
| 2004/0068288 A1 | 4/2004 | Palmer et al. |
| 2004/0220609 A1 | 11/2004 | Douk et al. |
| 2004/0225354 A1 | 11/2004 | Allen et al. |
| 2005/0010285 A1 | 1/2005 | Lambrecht et al. |
| 2005/0015048 A1 | 1/2005 | Chiu et al. |
| 2005/0015112 A1 | 1/2005 | Cohn et al. |
| 2005/0119688 A1 | 6/2005 | Bergheim |
| 2005/0261759 A1 | 11/2005 | Lambrecht et al. |
| 2006/0173490 A1 | 8/2006 | LaFontaine et al. |
| 2007/0106324 A1 | 5/2007 | Garner et al. |
| 2007/0179590 A1 | 8/2007 | Lu et al. |
| 2008/0033341 A1 | 2/2008 | Grad |
| 2008/0039786 A1 | 2/2008 | Epstein et al. |
| 2009/0018498 A1 | 1/2009 | Chiu et al. |
| 2009/0076409 A1 | 3/2009 | Wu et al. |
| 2009/0222035 A1 | 9/2009 | Schneiderman |
| 2011/0137399 A1 | 6/2011 | Chomas et al. |
| 2011/0288529 A1 | 11/2011 | Fulton |
| 2012/0116351 A1 | 5/2012 | Chomas et al. |
| 2012/0259206 A1 | 10/2012 | Roberts et al. |
| 2013/0079731 A1 | 3/2013 | Chomas et al. |
| 2013/0226166 A1 | 8/2013 | Chomas et al. |
| 2014/0207178 A1 | 7/2014 | Chomas et al. |

FOREIGN PATENT DOCUMENTS

| | | |
|---|---|---|
| WO | WO 99/16382 | 4/1999 |
| WO | WO 99/44510 | 9/1999 |
| WO | WO 01/41679 | 6/2001 |
| WO | WO 01/45592 | 6/2001 |
| WO | WO 01/49215 | 7/2001 |
| WO | WO 2004/043293 | 5/2004 |

OTHER PUBLICATIONS

U.S. Appl. No. 14/259,293, filed Apr. 23, 2014, Bryan Pinchuk et al.

Embolization II, Scientific Session 11, JVIR, Mar. 27, 2012.

Embolization procedure lowers levels of "hunger hormone," leads to weight loss, EurekAlert Public Release, Mar. 7, 2013.

First-In-Man Study of Left Gastric Artery Embolization for Weight Loss, Nicholas Kipshidze et al., ACC.13, E2056, JACC Mar. 12, 2013, vol. 61, Issue 10.

Left Gastric Embolization Leads to Weight Loss, Bariatriac News, Owen Haskins, Dec. 4, 2013.

Fusion Drug Delivery System-Novel Catheter/Stent Design for Targeted Drug Delivery, Gerschwind & Barnett, Non-Published US provisional patent application filed Sep. 17, 2007.

A Study of the Geometrical and Mechanical Properties of a Self-Expandig Metallic Stent—Theory and Experiment, Dr. Michael R. Jedwab, Claude O. Clerc, Journal of Applied Biomaterials, vol. 4, Issue 1, pp. 77-85, Spring 1993.

Finite Element Stent Design, M. De Beule, R. Van Impe, P. Verdonck, B. Verhegghe, Computer Methods in Biomechanics and Biomedical Engineering, 2005.

Catheter-Based Renal Sympathetic Denervation for Resistant Hypertension: a Multicentre Safety and Proof-of-Principle Cohort Study, Krum et al, The Lancet, 2009.

Renal Denervation as a Therapeutic Approach for Hypertension: Novel Implications for an Old Concept, Schlaich et al., Hypertension, Journal of the American Heart Association, 2009, 54:1195-1201.

Renal Sympathetic-Nerve Ablation for Uncontrolled Hypertension, Schlaich et al, The New England Journal of Medicine, 2009, pp. 932-934.

U.S. Appl. No. 14/330,456, filed Jul. 14, 2014, Chomas et al.

U.S. Appl. No. 61/266,068, filed Dec. 2, 2009, Chomas et al.

U.S. Appl. No. 61/382,290, filed Sep. 13, 2010, Chomas et al.

* cited by examiner

DYNAMIC MICROVALVE PROTECTION DEVICE

CROSS-REFERENCE TO RELATED APPLICATIONS

This application is a continuation of U.S. Ser. No. 13/306,105, filed Nov. 29, 2011, and now issued as U.S. Pat. No. 9,539,081, which is a continuation-in-part of U.S. Ser. No. 12/957,533, filed Dec. 1, 2010, and now issued as U.S. Pat. No. 8,696,698, which claims the benefit of U.S. Ser. No. 61/382,290, filed Sep. 13, 2010, and is also a continuation-in-part of U.S. Ser. No. 12/829,565, filed Jul. 2, 2010, and now issued as U.S. Pat. No. 8,500,775, which claims priority from U.S. Ser. No. 61/266,068, filed Dec. 2, 2009, all of which are hereby incorporated by reference herein in their entireties.

BACKGROUND OF THE INVENTION

1. Field of Invention

The present invention relates generally to a medical embolizing treatment method that utilizes a protection device to increase penetration of a treatment agent into targeted blood vessels and reduce reflux of the treatment agent into non-targeted vessels.

2. State of the Art

Embolization, chemo-embolization, and radio-embolization therapy are often clinically used to treat a range of diseases, such as hypervascular liver tumors, uterine fibroids, secondary cancer metastasis in the liver, pre-operative treatment of hypervascular menangiomas in the brain and bronchial artery embolization for hemoptysis. An embolizing agent may be embodied in different forms, such as beads, liquid, foam, or glue placed into an arterial vasculature. The beads may be uncoated or coated. Where the beads are coated, the coating may be a chemotherapy agent, a radiation agent or other therapeutic agent. When it is desirable to embolize a small blood vessel, small bead sizes (e.g., 10 µm-100 µm) are utilized. When a larger vessel is to be embolized, a larger bead size (e.g., 100 µm-900 µm) is typically chosen.

While embolizing agent therapies which are considered minimally or limited invasive have often provided good results, they have a small incidence of non-targeted embolization which can lead to adverse events and morbidity. An infusion microcatheter allows bi-directional flow. That is, the use of a microcatheter to infuse an embolic agent allows blood and the infused embolic agent to move forward in addition to allowing blood and the embolic agent to be pushed backward (reflux). Reflux of a therapeutic agent causes non-target damage to surrounding healthy organs. In interventional oncology embolization procedures, the goal is to bombard a cancer tumor with either radiation or chemotherapy. It is important to maintain forward flow throughout the entire vascular tree in the target organ in order to deliver therapies into the distal vasculature, where the therapy can be most effective. This issue is amplified in hypovascular tumors or in patients who have undergone chemotherapy, where slow flow limits the dose of therapeutic agent delivered and reflux of agents to non-target tissue can happen well before the physician has delivered the desired dose.

The pressure in a vessel at multiple locations in the vascular tree changes during an embolic infusion procedure. Initially, the pressure is high proximally, and decreases over the length of the vessel. Forward flow of therapy occurs when there is a pressure drop. If there is no pressure drop over a length of vessel, therapy does not flow downstream. If there is a higher pressure at one location, such as at the orifice of a catheter, the embolic therapy flows in a direction toward lower pressure. If the pressure generated at the orifice of a catheter is larger than the pressure in the vessel proximal to the catheter orifice, some portion of the infused embolic therapy travels up stream (reflux) into non-target vessels and non-target organs. This phenomenon can happen even in vessels with strong forward flow if the infusion pressure (pressure at the orifice of the catheter) is sufficiently high.

During an embolization procedure, the embolic agents clog distal vessels and block drainage of fluid into the capillary system. This leads to an increase in the pressure in the distal vasculature. With the increased pressure, there is a decrease in the pressure gradient and therefore flow slows or stops in the distal vasculature. Later in the embolization procedure, larger vessels become embolized and the pressure increases proximally until there is a system that effectively has constant pressure throughout the system. The effect is slow flow even in the larger vessels, and distally the embolic agent no longer advance into the target (tumor).

In current clinical practice, the physician attempts to infuse embolics with pressure that does not cause reflux. In doing this, the physician slows the infusion rate (and infusion pressure) or stops the infusion completely. The clinical impact of current infusion catheters and techniques is two fold: low doses of the therapeutic embolic is delivered and there is poor distal penetration into the target vessels.

Additionally, reflux can be a time-sensitive phenomenon. Sometimes, reflux occurs as a response to an injection of the embolic agent, where the reflux occurs rapidly (e.g., in the time-scale of milliseconds) in a manner which is too fast for a human operator to respond. Also, reflux can happen momentarily, followed by a temporary resumption of forward flow in the blood vessel, only to be followed by additional reflux.

FIG. 1 shows a conventional (prior art) embolization treatment in the hepatic artery 106. Catheter 101 delivers embolization agents (beads) 102 in a hepatic artery 106, with a goal of embolizing a target organ 103. It is important that the forward flow (direction arrow 107) of blood is maintained during an infusion of embolization agents 102 because the forward flow is used to carry embolization agents 102 deep into the vascular bed of target organ 103.

Embolization agents 102 are continuously injected until reflux of contrast agent is visualized in the distal area of the hepatic artery. Generally, since embolization agents 102 can rarely be visualized directly, a contrast agent may be added to embolization agents 102. The addition of the contrast agent allows for a visualization of the reflux of the contrast agent (shown by arrow 108), which is indicative of the reflux of embolization agents 102. The reflux may, undesirably, cause embolization agents 102 to be delivered into a collateral artery 105, which is proximal to the tip of catheter 101. The presence of embolization agents 102 in collateral artery 105 leads to non-target embolization in a non-target organ 104, which may be the other lobe of the liver, the stomach, small intestine, pancreas, gall bladder, or other organ.

Non-targeted delivery of the embolic agent may have significant unwanted effects on the human body. For example, in liver treatment, non-targeted delivery of the embolic agent may have undesirable impacts on other organs including the stomach and small intestine. In uterine fibroid treatment, the non-targeted delivery of the embolic agent may embolize one or both ovaries leading to loss of menstrual cycle, subtle ovarian damage that may reduce fertility, early onset of menopause and in some cases substantial damage to the ovaries. Other unintended adverse events include unilateral deep buttock pain, buttock necrosis, and uterine necrosis.

Often, interventional radiologists try to reduce the amount and impact of reflux by slowly releasing the embolizing agent and/or by delivering a reduced dosage. The added time, complexity, increased x-ray dose to the patient and physician (longer monitoring of the patient) and potential for reduced efficacy make the slow delivery of embolization agents suboptimal. Also, reducing the dosage often leads to the need for multiple follow-up treatments. Even when the physician tries to reduce the amount of reflux, the local flow conditions at the tip of the catheter change too fast to be controlled by the physician, and therefore rapid momentary reflux conditions can happen throughout infusion.

SUMMARY OF THE INVENTION

According to one aspect of the invention, a deployable apparatus is provided that is useful in an embolization procedure and which enables substantially unrestricted forward flow of blood in a vessel and reduces or stops reflux (regurgitation or backward flow) of embolization agents which are introduced into the blood.

In some embodiments, the deployable apparatus includes a delivery catheter having a valve fixedly coupled to the distal end thereof. An outer catheter is provided which extends over the valve during introduction to maintain the valve in a collapsed cylindrical configuration until the valve is advanced through the patient to the desired vascular destination. Once at the destination, the outer catheter is retracted from over the valve to permit expansion of the valve into an open state, as discussed below.

In other embodiments, the deployable apparatus includes a delivery catheter and a valve introducer which delivers a valve to a valve seat at the distal end of the delivery catheter during the embolization procedure. No outer catheter is required. A valve introducer maintains the distal end of the valve in a closed configuration, and a push wire is abutted against the proximal end of the valve and used to push the valve out of the valve introducer and through the delivery catheter. The valve is advanced by the push wire to the valve seat located at the distal end of a delivery catheter. Once the valve seat captures a proximal portion of the valve to lock the valve at the distal end of the delivery catheter, the push wire is then withdrawn from the delivery catheter to provide an apparatus with enhanced fluid flow through the delivery catheter. In certain embodiments a pull member is coupled to the valve to release the lock between the valve and valve seat and permit retraction of the valve into the delivery catheter after the embolic agent has been dispensed.

The deployable valve includes a plurality of filaments which cross over each other (i.e., are braided) and which have a spring bias to assume a preferred crossing angle relative to each other. In a first state, the valve is preferably kept in a cylindrical arrangement with a diameter substantially equal to the diameter of the delivery catheter. In a second state, the valve is free to open due to the spring bias in the filaments. In the second state, with the proximal end of the valve attached to the delivery catheter, in the bloodstream, if the blood is not flowing distally past the valve, the valve assumes a substantially frustoconical shape. The distal end of the valve is intended to make contact with the walls of the vessel in which it is deployed when blood is not flowing distally past the valve.

In some embodiments, the valve, while enabling substantially unrestricted forward flow in a vessel and reducing or stopping reflux of embolization agents, allows the reflux of blood or contrast agent. In other embodiments, the valve, while enabling substantially unrestricted forward flow in a vessel and reducing or stopping reflux of embolization agents, also reduces or stops backward flow of blood.

According to one aspect of the invention, the valve has a radial force of expansion when in the undeployed state of less than 40 mN.

According to another aspect of the invention, the valve has a time constant of expansion from the cylindrical arrangement to the fully-open position when in a static fluid having a viscosity of approximately 3.2 cP of between 1.0 and 0.01 seconds, and more preferably between 0.50 and 0.05 seconds.

According to a further aspect of the invention, the valve has a Young's modulus of elasticity that is greater than 100 MPa.

According to yet another aspect of the invention, the preferred crossing angle of the valve filaments is approximately 130 degrees.

According to even another aspect of the invention, the filaments of the valve are selected to be of a desired number and diameter such that in an open position, they are capable of trapping embolization agents. By way of example only, the filaments of the valve are selected so that in an open position they present a pore size of 500 μm and are thus capable of preventing reflux of embolizing agent such as beads having a size larger than 500 μm. As another example, the filaments of the valve are selected so that in an open position they present a pore size of 250 μm and are thus capable of preventing reflux of embolizing agent having a size larger than 250 μm.

In one embodiment, the valve filaments are coated with a filter which is formed and attached to the filaments according to any desired manner, such as by spraying, spinning, electrospinning, bonding with an adhesive, thermally fusing, melt bonding, or other method. The filter is preferably arranged to have a desired pore size, although it will be appreciated that the pore size may be non-uniform depending upon the technique in which the filter is formed and attached. By way of example, the pore size of the filter may be approximately 40 μm such that embolizing agents having a characteristic size of more than 40 μm are prevented from refluxing past the valve. By way of another example, the pore size of the filter may be approximately 20 μm such that embolizing agents having a characteristic size of more than 20 μm are prevented from refluxing past the valve. In both cases, blood cells (which have a characteristic size smaller than 20 μm), and contrast agent which has a molecular size smaller than 20 μm will pass through the filter and valve.

According to an additional aspect of the invention, when in a fully-open position where the filaments assume the preferred crossing angle, the valve is adapted to have a distal diameter which is at least twice the diameter of the delivery catheter, and preferably at least five times the diameter of the delivery catheter.

In one embodiment, the filaments are all formed from a polymer. In another embodiment, one or more of the filaments is formed from stainless steel, platinum or platinum-iridium.

In an embodiment where one or more filaments are formed from a polymer, the filaments that are formed from the polymer are preferably melted at their proximal end into the delivery catheter.

The valve may be deployed in any of several manners. Thus, by way of example only, in appropriate embodiments, an outer catheter or sleeve extending over the delivery catheter may be used to keep the valve in an undeployed state, and the outer catheter or sleeve may be pulled backward relative to the delivery catheter in order to deploy the valve. Where an outer catheter or sleeve is utilized, the valve may be captured and returned to its undeployed position by moving the delivery catheter proximally relative to the outer catheter or sleeves.

As another example, the distal end of the valve may be provided with loops which are adapted to engage a guidewire which extends through and distal the distal end of the delivery catheter and through the distal loops of the valve. When the guidewire is withdrawn proximally, the valve deploys.

As another example, a knitted sleeve with a control thread can be provided to cover the valve. The control thread, when pulled, causes the knitted sleeve to unravel, thereby releasing the valve.

As yet another example, when no outer catheter is provided, the valve may be deployed by advancement through the delivery catheter and engagement between a valve seat at the distal end of the delivery catheter and corresponding mating structure at the proximal end of the valve. When the valve is engaged in the valve seat, the valve filaments extend distally of the delivery catheter and without further constraint on dynamic operation of the valve.

In addition, the valve may be retracted in any of several manners. Where an outer catheter is provided, the outer catheter and delivery catheter are movable relative to each other to cause the outer catheter to collapse the valve. In some embodiment where no outer catheter is provided, the valve may be released from the distal end of the delivery catheter and withdrawn, either so that it is drawn completely into the delivery catheter or completely withdrawn from the proximal end of the delivery catheter. One or more pull wires, including a braided construct may be attached to the valve to aid in such withdrawal of the valve. It is also appreciated that the valve may be withdrawn from the patient in a deployed state, if necessary.

In operation, the deployable apparatus operates as a one-way infusion system which allows forward flow of blood and infusate, but dynamically blocks reverse flow of embolics and most of the fluid that would flow backward during a reflux condition. During infusion in high downstream flow conditions, the valve of the deployable apparatus collapses and allows flow into downstream vascular branches. Any time the pressure in the orifice of the catheter (inside the expandable valve) increases higher than the pressure in the blood vessel, the expandable valve immediately opens and seals to the blood vessel wall, thus blocking upstream reflux of embolics. It is important to note that pressure is communicated throughout the vasculature at the speed of sound in blood (1540 m/s). Since the expandable valve responds to pressure changes, it reacts far faster than the flow rates of embolics in the blood (0.1 m/s).

Thus, the expandable valve provides a mechanism for the physician to increase pressure at the distal end of the catheter without risking reflux. This allows the physician to drive greater distal penetration of embolics than would be possible with a standard catheter. The apparatus may be used to either infuse a greater amount of therapy, enhance distal penetration of the therapy, or both. The device may also be used to infuse a small bolus of therapy, and then a larger infusion of saline to create greater distal penetration of the relatively small dose of therapy.

The design of the expandable valve filter may also be such that proteins in the blood almost immediately fill the pores of the filter valve once the valve is deployed into the vessel. The coatings provide a safety feature of the valve, such that while the pores can be filled with the blood proteins at pressures at or greater than the safe blood vessel pressures. However, once the pressure in the vessel exceeds a threshold pressure the coating facilitates release of the proteins from at the pores such that the pores are opened to thereby reduce intravessel pressure to a safe level. With the pores opened, blood can regurgitate through the pores of the filter valve, but the embolic agent continues to be contained at the high pressure side of the filter valve, as the embolic agent is too large to pass through the pores.

BRIEF DESCRIPTION OF DRAWINGS

Prior art

DETAILED DESCRIPTION OF THE PREFERRED EMBODIMENTS

Figure 1:
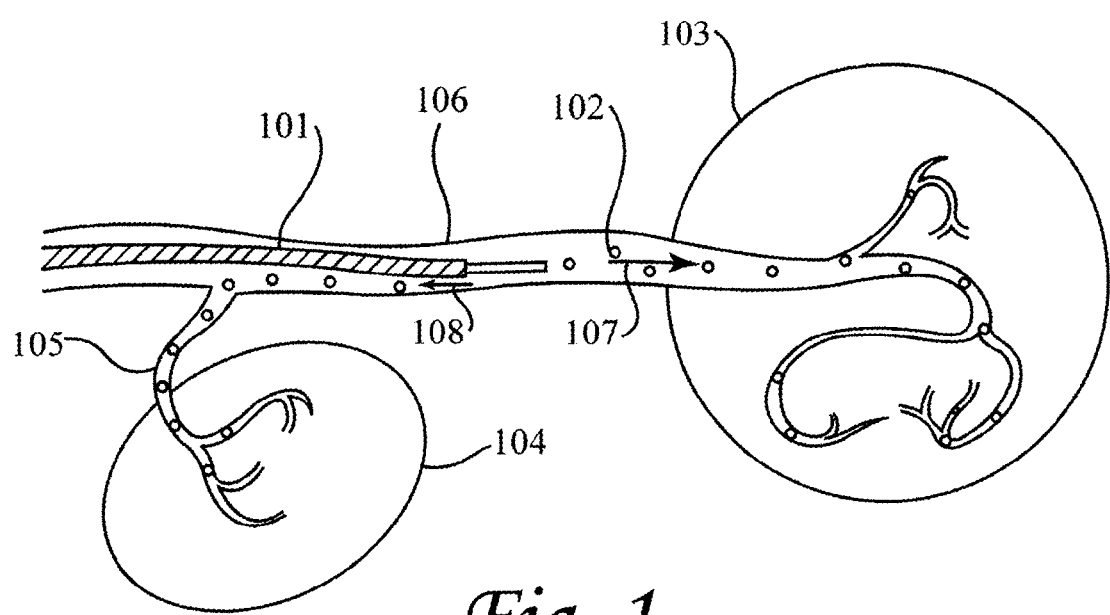
FIG. 1 shows a conventional embolizing catheter in a hepatic artery with embolizing agent refluxing into a non-targeted organ.
Figure 2A:
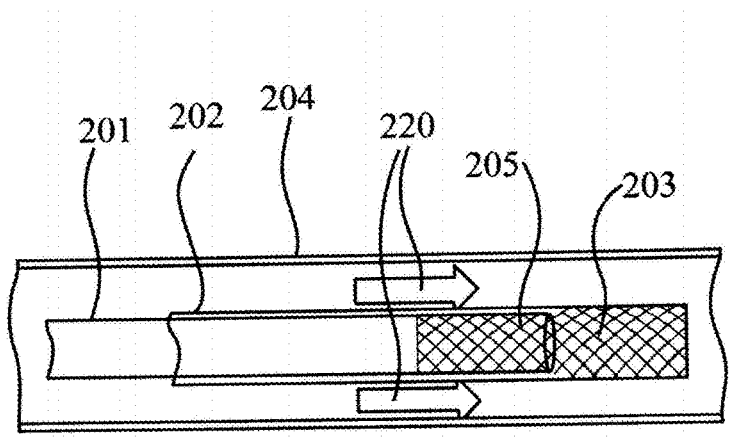
FIGS. 2A-2C are schematic diagrams of a first exemplary embodiment of an apparatus of the invention respectively in an undeployed state, a deployed partially open state with blood passing in the distal direction, and a deployed fully open state where the blood flow is static.
Figure 2B:
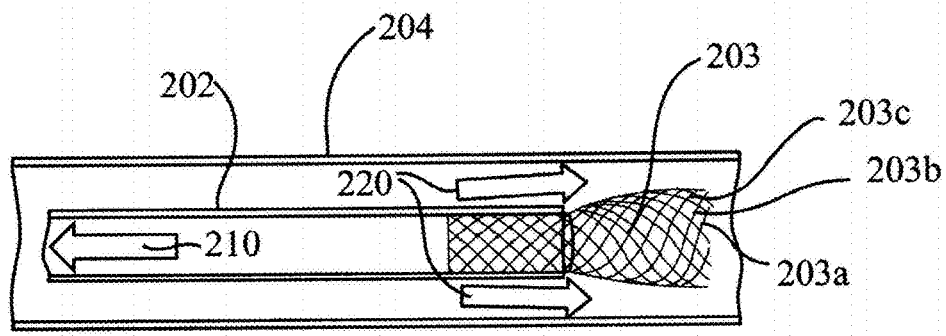
Figure 2C:
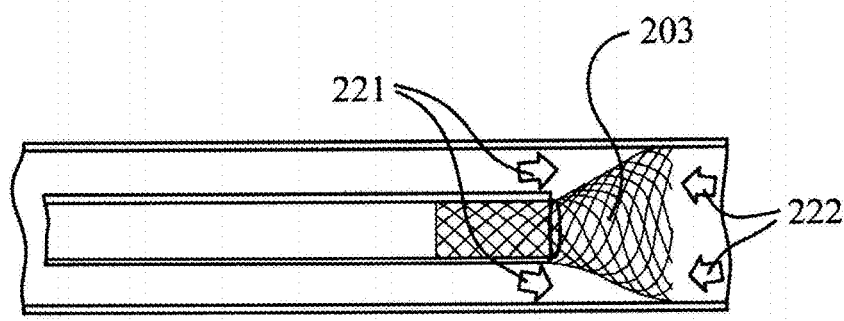

A first exemplary embodiment of the invention is seen in FIGS. 2A-2C. It is noted that FIGS. 2A-2C are not shown to relative size but rather are shown for purposes of explanation. In FIGS. 2A-2C a delivery catheter 201 having a proximal end (not shown) and a distal end 205 is shown positioned within an artery 204. The delivery catheter 201 is adapted for delivery of an embolizing agent from outside the body of the patient (not shown) to a target vessel (artery or vein) in the patient. Attached to the distal end 205 of the catheter 201 is an exemplary embodiment of a valve 203 shown having multiple filaments 203a, 203b, 203c, . . . which are preferably braided and can move relative to each other. As discussed hereinafter, the filaments are spring biased (i.e., they have "shape memory") to assume a desired crossing angle relative to each other so that the valve can assume a substantially frustoconical shape (it being noted that for purposes herein the term "substantially frustoconical" should be understood to include not only a truncated cone, but a truncated hyperboloid, a truncated paraboloid, and any other shape which starts from a circular proximal end and diverges therefrom). Around the catheter 201 is an outer catheter or sleeve 202 which is movable over the delivery catheter 201 and valve 203. If desired, the outer catheter or sleeve 202 can extend the entire length of the delivery catheter. Where the outer catheter or sleeve 202 extends along the entire length of the delivery catheter, it has a proximal end (not shown) which extends proximally and which can be controlled by a practitioner from outside the body of the patient. Alternatively, the outer catheter or sleeve 202 extends only over the distal end of the delivery catheter 201 and valve 203, but is controlled by a control element which extends proximally and which can be controlled by a practitioner from outside the body of the patient.

As seen in FIG. 2A, when the outer catheter or sleeve 202 extends over the valve 203, the multiple filaments are forced into a cylindrical shape. Thus, FIG. 2A shows the braid valve in an undeployed cylindrical state, with the braid filaments 203a, 203b, 203c . . . attached to a distal end of a catheter 205 and covered by the sleeve 202. Catheter 201 is positioned within an artery 204 that has forward blood flow in the direction of arrows 220. Such a condition occurs when the pressure upstream is greater than the pressure downstream. As seen in FIG. 2B, upon retraction of the sleeve 202 in the direction of arrow 210, the non-constrained portion of the valve 203 is freed to expand radially (and retract longitudinally) in accord with its bias towards its shape memory position. Given the same pressure conditions, the valve does not open more completely; i.e., it does not expand across the vessel wall. More particularly, at pressure greater than 10 mmHg causing the blood flow indicated by arrows 220 and with no countervailing pressure, the valve is prevented from opening more completely. As a result, the valve 203 is maintained in a condition where it permits downstream blood flow and is not sufficiently open to block blood flow in the distal downstream or proximal upstream 'reflux' directions.

FIG. 2C shows the valve 203 where there is blood pressure on the proximal side of the valve, but such pressure is lower than a countervailing pressure within the valve; i.e., such as during delivery of embolic agents through catheter 201 and past the valve 203. In fact, such pressure may be significantly higher than the blood pressure. In the fully deployed arrangement of FIG. 2C, the braid valve acts as a filter to stop embolic agents from flowing proximal the valve. However, as discussed, depending upon the pore size of the braid valve 203, blood and contrast agent may be permitted to flow backward through the valve and around the catheter 201 while preventing backflow of embolic agents.

It should be appreciated by those skilled in the art that the catheter 201 can be any catheter known in the art. Typically, the catheter will be between two and eight feet long, have an outer diameter of between 0.67 mm and 3 mm (corresponding to catheter sizes 2 French to 9 French), and will be made from a liner made of fluorinated polymer such as polytetrafluoroethylene (PTFE) or fluorinated ethylene propylene (FEP), a braid made of metal such as stainless steel or titanium, or a polymer such as polyethylene terephthalate (PET) or liquid crystal polymer, and an outer coating made of a polyether block amide thermoplastic elastomeric resin such as PEBAX®, polyurethane, polyamide, copolymers of polyamide, polyester, copolymers of polyester, fluorinated polymers, such as PTFE, FEP, polyimides, polycarbonate or any other suitable material, or any other standard or specialty material used in making catheters used in the bloodstream. Sleeve or outer catheter 202 is comprised of a material capable of holding valve braid 203 in a cylindrical configuration and capable of sliding over the valve braid 203 and the catheter 201. Sleeve or outer catheter 202 can be comprised of polyurethane, polyamide, copolymers of polyamide, polyester, copolymers of polyester, fluorinated polymers, such as PTFE, FEP, polyimides, polycarbonate or any other suitable material. The sleeve or outer catheter may also contain a braid composed of metal such as stainless steel or titanium, or a polymer such as PET or liquid crystal polymer, or any other suitable material. The wall thickness of sleeve or outer catheter 202 is preferably in the range of 0.05 mm to 0.25 mm with a more preferred thickness of 0.1 mm-0.15 mm.

The valve 203 is composed of one, two, or more metal (e.g., stainless steel or Nitinol) or polymer filaments, which form a substantially frustoconical shape when not subject to outside forces. Where polymeric filaments are utilized, the filaments may be composed of PET, polyethylene-napthalate (PEN), liquid crystal polymer, fluorinated polymers, nylon, polyamide or any other suitable polymer. If desired, when polymeric filaments are utilized, one or more metal filaments may be utilized in conjunction with the polymeric filaments. According to one aspect of the invention, where a metal filament is utilized, it may be of radio-opaque material such that it may be tracked in the body. The valve is capable of expanding in diameter while reducing in length, and reducing in diameter while expanding in length. The valve is preferably composed of shape memory material that is formed and set in a large diameter orientation. As previously mentioned, the valve is preferably held in a small diameter orientation until it is released, and when released by removing the sleeve or other restricting component 202, the distal end of the valve expands to a larger diameter. Where the valve is comprised of multiple filaments, it is preferred that the filaments not be bonded to each other along their lengths or at their distal ends so to enable the valve to rapidly automatically open and close in response to dynamic flow conditions.

In the preferred embodiment, the valve is constrained only at its proximal end where it is coupled to the catheter body, while the remainder of the valve can either be constrained (retracted state) by a sleeve or catheter, or partially unconstrained (partially deployed state) or completely unconstrained (completely deployed state). When in the partially or completely unconstrained conditions, depending upon the flow conditions in the vessel, the valve may either reach the walls of the vessel or it may not.

As previously mentioned, the valve diameter should automatically change in response to local pressure conditions so as to permit forward flow when the pressure proximal of the valve is higher than the pressure within and distal of the valve, but capture embolic agents during brief or prolonged periods of when the pressure within and distal of the valve is higher than proximal of the valve. For simplicity, the valve can be considered to exist in two conditions. In a "closed" condition, the valve is not sealed against the vessel wall and blood may flow around in at least a proximal to distal direction. In an "open" condition, the valve expands against the vessel wall and blood must pass through the valve if it is to flow past the valve within the vessel in either direction; in the "open" condition embolic agent is prevented from passing downstream (or in a distal to proximal direction) of the valve.

Three parameters help define the performance and novel nature of the valve: the radial (outward) force of the valve, the time constant over which the valve changes condition from closed to open, and the pore size of the valve.

In a preferred embodiment, the valve expands fully to the vessel wall (i.e., reaches an open condition) when the pressure at the orifice of the catheter and within the valve is greater than the blood pressure (FIG. 2C), and remains in a closed condition when blood is flowing distally with pressure greater than the pressure within and distal of the valve (FIG. 2B). In addition, when the radial force of expansion on the valve (i.e., the expansion force of the valve itself in addition to the force of pressure in the distal vessel over the distal surface area of the valve) is greater than the radial force of compression on the valve (i.e., force of pressure in the proximal vessel over the proximal surface area of the valve), the valve fully expands to the configuration shown in FIG. 2C so that the valve assumes the open configuration. Thus, as seen, according to one aspect of the invention, the radial force of expansion of the valve is chosen to be low (as described in more detail below) so that normal blood flow in the downstream distal direction will prevent the valve from reaching the open condition. This low expansion force is different than the expansion forces of prior art stents, stent grafts, distal protection filters and other vascular devices, which have significantly higher radial forces of expansion.

The radial force of expansion of a braid is described by Jedwab and Clerc (*Journal of Applied Biomaterials*, Vol. 4, 77-85, 1993) and later updated by DeBeule (DeBeule et al., *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0} \quad K_2 = \frac{2\cos^2\beta_0}{D_0} \quad K_3 = \frac{D_0}{\cos\beta_0}$$

and I and $I_p$ are the surface and polar moments of inertia of the braid filaments, E is the Young's modulus of elasticity of the filament, and G is the shear modulus of the filament. These material properties along with the initial braid angle ($\beta_0$), final braid angle ($\beta$), stent diameter ($D_0$), and number of filaments (n) impact the radial force of the braided valve.

In one embodiment, with a valve arrangement as shown in FIGS. 2A-2C, the valve 203 is composed of twenty-four polyethylene terephthalate (PET) filaments 203a, 203b, . . . , each having a diameter of 0.1 mm and pre-formed to an 8 mm diameter mandrel and a braid angle of 130° (i.e., the filaments are spring-biased or have a shape memory to assume an angle of 130° relative to each other when the valve assumes a fully deployed state and opens in a frustoconical configuration). The filaments preferably have a Young's modulus greater than 200 MPa, and the valve preferably has a radial force of less than 40 mN in the fully deployed position (i.e., where the filaments assume their shape memory). More preferably, the valve has a radial force in the fully deployed position of less than 20 mN, and even more preferably the valve has a radial force of approximately 10 mN (where the term "approximately" as used herein is defined to mean±20%) in the deployed position. Where the valve includes a filter as well as the braided filaments (as will be discussed hereinafter with respect to FIGS. 3A and 3B), the braid component preferably has a radial force of less than 20 mN in the fully deployed position, and more preferably a radial force of less than 10 mN, and even more preferably a radial force of approximately 5 mN. This compares to prior art embolic capture devices such as the ANGIOGUARD® (a trademark of Cordis Corporation), and prior art Nitinol stents and stent-grafts which typically have radial forces of between 40 mN and 100 mN in their fully deployed positions.

According to one aspect of the invention, the valve opens and closes sufficiently quickly to achieve high capture efficiency of embolic agents in the presence of rapidly changing pressure conditions. More particularly, any time the pressure at the distal opening of the catheter (inside the expandable valve) increases higher than the pressure in the blood vessel, the expandable valve substantially immediately opens and seals to the blood vessel wall, thus blocking refluxing embolics. It is important to note that pressure is communicated throughout the vasculature at the speed of sound in blood (1540 m/s) and that the valve opens and closes in in response to pressure changes within the blood vessel. Since the expandable valve responds to pressure changes, it reacts far faster than the flow rates of embolics in the blood (0.1 m/s) thereby preventing reflux of any embolics.

In one embodiment, when subject to the infusion pressure at the catheter distal end, the valve moves from a fully closed (undeployed) position to a fully open position in a static fluid (e.g., glycerin) having a viscosity approximately equal to the viscosity of blood (i.e., approximately 3.2 cP) in 0.067 second. For purposes herein, the time it takes to move from the fully closed position to the fully open position in a static fluid is called the "time constant". According to another aspect of the invention, the valve is arranged such that the time constant of the valve in a fluid having the viscosity of blood is between 0.01 seconds and 1.00 seconds. More preferably, the valve is arranged such that the time constant of the valve in a fluid having the viscosity of blood is between 0.05 and 0.50 seconds. The time constant of the valve may be adjusted by changing one or more of the parameters described above (e.g., the number of filaments, the modulus of elasticity of the filaments, the diameter of the filaments, etc.).

As will be appreciated by those skilled in the art, the braid geometry and material properties are intimately related to the radial force and time constant of the valve. Since, according to one aspect of the invention, the valve is useful in a variety of arteries of different diameters and flow conditions, each implementation can have a unique optimization. By way of example only, in one embodiment, the valve has ten filaments, whereas in another embodiment, the valve has forty filaments. Preferably, the filament diameter is chosen in the range of 0.025 mm to 0.127 mm, although other diameters may be utilized. Preferably, the pitch angle (i.e., the crossing angle assumed by the filaments in the fully open position—the shape memory position) is chosen in the range of 100° to 150°, although other pitch angles may be used. Preferably, the Young's modulus of the filament is at least 100 MPa, and more preferably at least 200 MPa.

According to another aspect of the invention, the valve is chosen to have a pore size which is small enough to capture (filter) embolic agents in the blood stream as the blood passes through the valve. Where large embolic agents (e.g., 500 µm) are utilized, it may be possible for the filaments of the valve to act directly as a filter to prevent embolic agents from passing through the valve (provided the filaments present pores of less than, e.g., 500 µm). Alternatively, a filter may be added to the filament structure. Such a separate filter is particularly useful where smaller embolic agents are utilized.

Figure 3A:
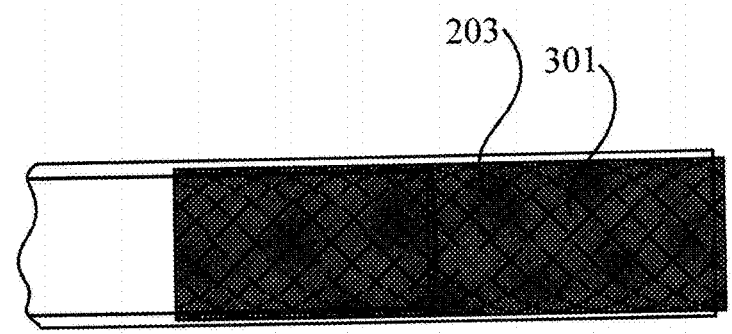
FIGS. 3A and 3B are schematic diagrams of an exemplary embodiment of a valve having a braid component that is covered by a filter component in respectively an undeployed state and a deployed state.
Figure 3B:
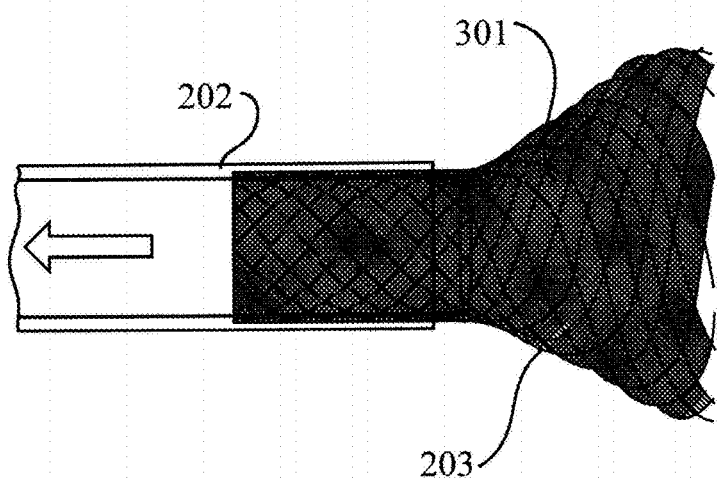

FIG. 3A shows a braid valve 203 at the distal end of a catheter 201 and having a filter 301 that is added to the braid structure 203. The filter can be placed onto the braid by spraying, spinning, electrospinning, bonding with an adhesive, thermally fusing, mechanically capturing the braid, melt bonding, or any other desired method. The filter can either be a material with pores such as ePTFE, a solid material that has pores added such as polyurethane with laser drilled holes, or the filter can be a web of very thin filaments that are laid onto the braid. Where the filter 301 is a web of thin filaments, the characteristic pore size of the filter can be determined by attempting to pass beads of different diameters through the filter and finding which diameter beads are capable of passing through the filter in large quantities. The very thin filaments can be spun onto a rotating mandrel according to U.S. Pat. No. 4,738,740 with the aid of an electrostatic field or in the absence of an electrostatic field or both. The filter thus formed can be adhered to the braid structure with an adhesive or the braid can be placed on the mandrel and the filter spun over it, or under it, or both over and under the braid to essentially capture it. The filter can have some pores formed from spraying or electrospinning and then a secondary step where pores are laser drilled or formed by a secondary operation. In the preferred embodiment a material capable of being electrostatically deposited or spun is used to form a filter on the braid, with the preferred material being capable of bonding to itself. The filter may be made of polyurethane, pellethane, polyolefin, polyester, fluoropolymers, acrylic polymers, acrylates, polycarbonates, or other suitable material. The polymer is spun onto the braid in a wet state, and therefore it is desirable that the polymer be soluble in a solvent. In the preferred embodiment, the filter is formed from polyurethane which is soluble in dimethylacetamide. The polymer material is spun onto the braid in a liquid state, with a preferred concentration of 5-10% solids for an electrostatic spin process and 15-25% solids for a wet spin process. FIG. 3B shows the valve in the deployed state, with outer catheter 202 retracted proximally (as indicated by the arrow) where the braid 203 and the filter 301 are expanded.

According to one aspect of the invention, the filter 301 has a characteristic pore size between 10 µm and 500 µm. More preferably, the filter 301 has a characteristic pore size between 15 µm and 100 µm. Even more preferably, the filter 301 has a characteristic pore size of less than 40 µm and more preferably between 20 µm and 40 µm. Most desirably, the filter 301 is provided with a characteristic pore size that will permit pressurized blood and contrast agent to pass therethrough while blocking passage of embolizing agent therethrough. By allowing regurgitating blood and contrast agent to pass through the filter in a direction from distal the valve toward the proximal end of the valve, the contrast agent may be used to indicate when the target site is fully embolized and can serve to identify a clinical endpoint of the embolization procedure. Therefore, according to one aspect of the invention, the valve allows the reflux of the contrast agent as an indicator of the clinical endpoint while preventing the reflux of the embolization agents at the same time. In addition, by allowing blood to flow back through the filter material, even at a relatively slow rate, backpressure on the distal side of the valve can be alleviated.

The filter 301 is also preferably provided with a hydrophilic coating, hydrophobic coating, or other coating that affects how proteins within blood adhere to the filter and specifically within the pores of the filter. More specifically, the coating is resistant to adhesion of blood proteins. One coating that has been used successfully is ANTI-FOG COATING 7-TS-13 available from Hydromer, Inc. of Branchburg, N.J., which can be applied to the filter by, e.g., dipping, spraying, roll or flow coating.

By appropriate design of the pore size and use of an appropriate coating, proteins in the blood will almost immediately fill the pores during use. The proteins on the coated porous filter operate as a pressure safety valve, such that the pores are filled with the proteins when subject to an initial fluid pressure greater than the blood vessel pressure, but the proteins are displaced from the pores and the pores are opened to blood flow at higher pressures such as a designated threshold pressure. The designated threshold pressure is determined to prevent damage to the tissue and organs, and injury to the patient. Thus, this system allows a pressure greater than the vessel pressure while limiting very high pressures which may be unsafe to the patient. As such, the system provides pressure regulation which is not possible with other occlusive devices, including balloons. Notwithstanding the advantage of the above, it is not a requirement of the invention that the filter be constructed to allow either blood or contrast agent to pass through in the upstream 'reflux' direction under any determined pressure.

According to one aspect of the method of the invention, the valve is capable of endovascular deployment. The valve is preferably coupled to the distal end of a catheter. When the distal end of the catheter is in the correct location for treatment, the valve is deployed. Preferably, with the valve deployed, embolization agents are delivered under pressure distally through the catheter and into the vessel. As discussed above, delivery of the embolization agents in this manner will result in a pressure change that initially causes higher pressure within the valve than upstream of the valve, thereby resulting in the valve rapidly expanding to assume an open position. During such expansion, the valve expands from an initial diameter (non-deployed or non-pressured position) to a final diameter (its open position) which is preferably at least twice, and more typically four to ten times the outer diameter of the catheter. In its open position, the valve stops embolization agents from traveling upstream past the valve (between the catheter wall and the vessel wall) in a proximal 'reflux' direction. According to one aspect of the invention, the valve is preferably capable of being retracted into its closed position after the embolization treatment procedure is completed.

It is important to note that the valve is a dynamic element that opens and closes based on local pressure conditions. In normal blood flow conditions when no fluid is infused through the catheter, the pressure within the valve and downstream of the valve is lower than the vascular pressure upstream of the valve. This pressure differential is sufficient to overcome the weak biasing force of the valve, thereby forcing the valve into a partially closed position such that it does not contact the vascular wall and thereby permits fluid to flow in the downstream direction around the outside of the valve. When the fluid pressure inside and outside of the valve is substantially the same, as may occur during the cyclic blood pressure and related flow conditions as the heart beats, the biasing force of the valve filaments causes the valve to expand into a partially expanded, but still 'closed' position; i.e., the valve does not reach the vessel wall. In addition, this may occur, e.g., when a priming fluid is infused through the catheter and valve at a similar pressure to the blood pressure. When higher pressure is generated through the open the distal end of the catheter and inside of the valve, such as may occur when the embolic infusate is injected under pressure into the catheter, the valve rapidly enters a fully open position in which it is in full contact with the vascular wall, thereby preventing reflux of embolizing agents.

Figure 52:
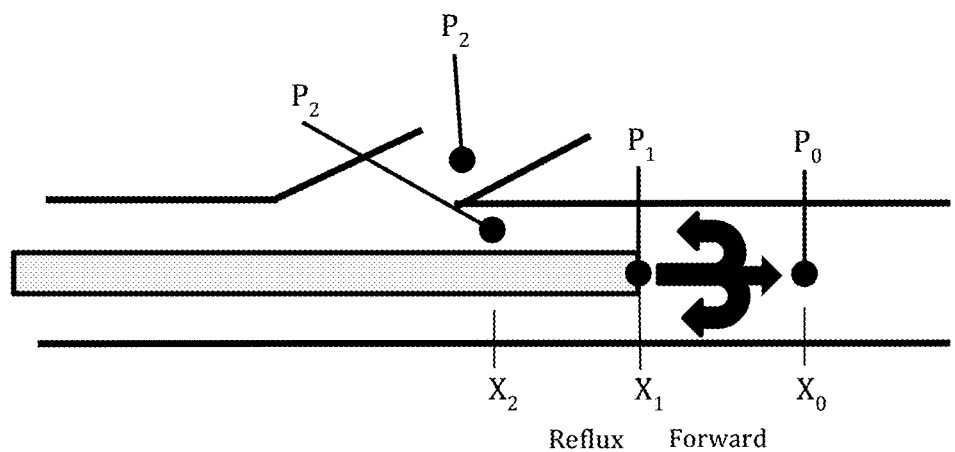
FIG. 52 is a schematic diagram of a prior art therapy infusion catheter infusing an embolic agent into a vessel.
Figure 53:
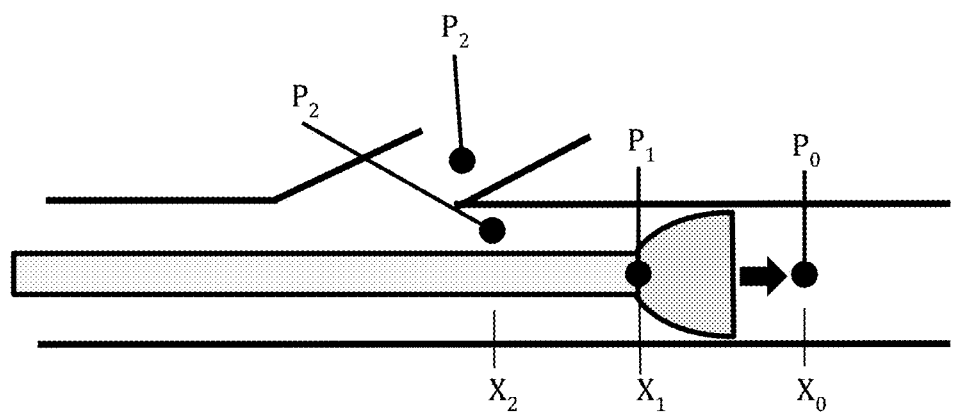
FIG. 53 is a schematic diagram of a therapy infusion apparatus according to the invention infusing an embolic agent into a vessel

By way of example, referring to FIG. 52, a prior art infusion catheter is shown. Embolic agent infused through the catheter will reflux upstream of $X_1$ if either or both the downstream vessel pressure at $P_0$ or the catheter pressure at $P_1$ is greater than the upstream vessel pressure $P_2$. This will result in embolic agent traveling upstream past the opening of the catheter and to a location $X_2$, which may include upstream and branched locations at which the agent may have deleterious effect. By contrast, turning now to FIG. 53, the system of the invention is shown. In this system, embolic agent is infused through the catheter. Provided the pressure $P_1$ within the catheter is greater than the vessel pressures at $P_2$, the valve will substantially fully and immediately open. This prevents reflux of the embolic agent to a location $X_2$ and constrains the agent to downstream flow toward $X_0$.

Figure 54:
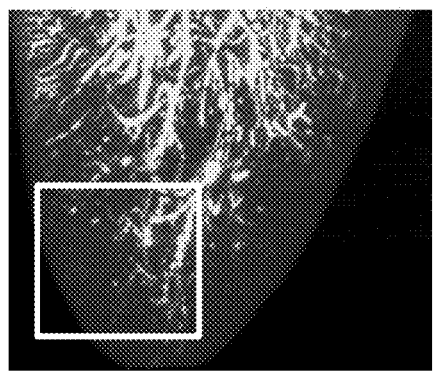
FIGS. 54-55 are photographs showing the penetration of an embolic agent (by visualization of a contrast agent) infused under standard prior art catheterization techniques, with FIG. 55 being an enlargement of the area highlighted in FIG. 54.
Figure 56:
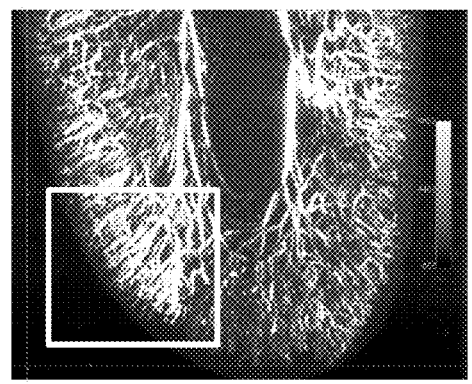
FIGS. 56-57 are photographs showing the penetration of an embolic agent (by visualization of a contrast agent) infused under the systems and techniques of the invention, with FIG. 57 being an enlargement of the area highlighted in FIG. 56.
Figure 55:
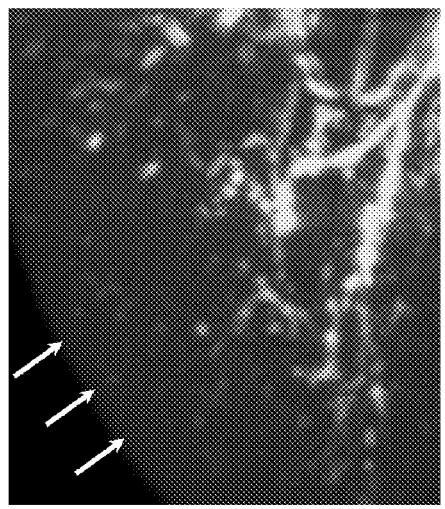
Figure 57:
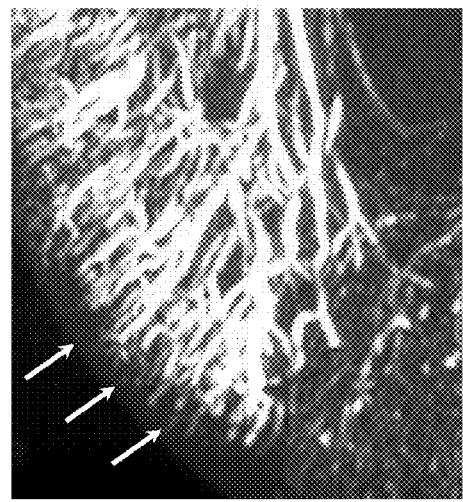

In addition, because the valve opens to prevent reflux of the embolic agent, significantly higher pressures can be applied at the catheter. At such higher infusion pressures, (1) a larger bolus of embolic agent can be infused, (2) the embolic agent can be driven downstream with greater distal penetration than otherwise possible with a standard catheter, and (3) or both. This effect is clearly shown in the results of an animal study in which one exemplar organ, pig kidneys, were infused with 40 μm tantalum beads (which are visible under X-rays) by each of a standard catheter and with the system of the invention. The kidney vasculature is hierarchical toward the cortex; i.e., larger vessels are located toward the center and smaller distal vessels branch outward toward the periphery. After infusion, the kidneys were imaged under Micro CT, which has a resolution of 50 μm and is highly sensitive to the tantalum beads. Referring to FIGS. 54-55, the images indicate that the agent did not penetrate into the smaller distal branches and instead remained in the medium sized vessels. Presumably, this is because insufficient pressure could be applied via the catheter to overcome the backpressure from the rapidly filling smaller vessels, and instead the pressure from the infusion catheter was equalized upstream. In contrast, referring to FIGS. 56-57, the images indicate significantly deeper penetration, out to the peripheral small vessels. The system allows the embolic to be applied under significant pressure to achieve such penetration. Further, the apparatus may be used to infuse a bolus of therapy, and then a large infusion of saline under pressure to create greater distal penetration of a small dose of therapy. This is not done with prior art systems out of concern for reflux.

It is recognized that in the open state, proteins in the blood may rapidly fill the pores of the filter valve. However, as discussed above, should a threshold pressure be reached, the filter valve is designed to permit the blood to reflux through the pores of the filter valve while still blocking the passage of the embolic agent. An exemplar threshold pressure is 180 mmHg on the distal surface of the filter valve, although the device can be designed to accommodate other threshold pressures. Such can be effected, at least in part, by the use of an appropriate coating on the filter that facilitates removal of the blood proteins from within the filter pores when subject to threshold pressure. This prevents the vessel in which the device is inserted from being subject to a pressure that could otherwise result in damage. Nevertheless, it is not necessary that blood and contrast agent be permitted to reflux through the valve.

According to one aspect of the invention, deployment of the valve is controlled from the proximal end of the catheter. In some embodiments, a control wire or a set of two or more control wires extending from the proximal end of the catheter to the distal end of the catheter may be used and controlled by the practitioner to deploy and optionally retract the valve. In some embodiments, a control thread extending from the proximal end of the catheter to the distal end of the catheter is used to unravel fabric covering the valve in order to deploy the valve. In some embodiments, an outer catheter that extends the length of the catheter to which the valve is coupled, covers the valve and during deployment is pulled backward to allow the valve to expand. In some embodiments, an outer sleeve that is coupled to a control element that extends the length of the catheter, covers the valve and during deployment is pulled backward by the control element to allow the valve to expand. In some embodiments, the valve is coupled to a guidewire, and removal of the catheter guidewire initiates deployment of the valve. The control wires, threads, sleeves, etc. may be of standard length, ranging, for example, from 60 cm to 240 cm long.

Figure 4A:
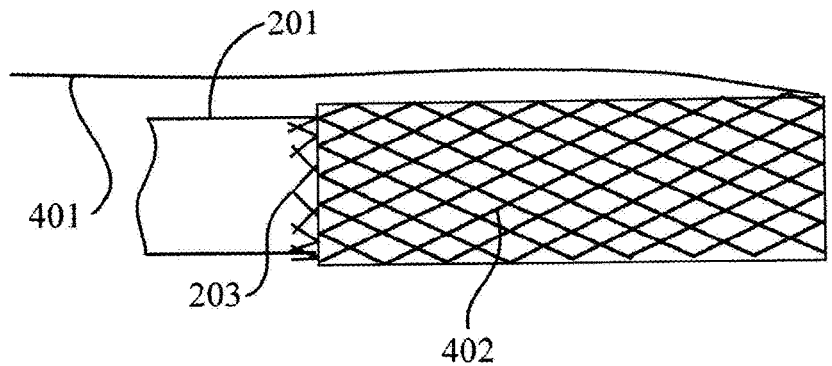
FIGS. 4A-4C are schematic diagrams of the exemplary embodiment of a valve of FIGS. 3A and 3B covered by a weft knit respectively in an undeployed state, a partially deployed state, and a more fully deployed state.
Figure 4B:
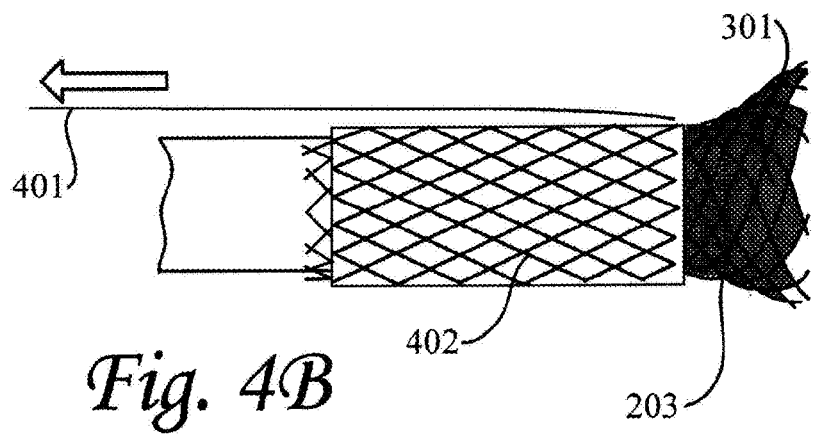
Figure 4C:
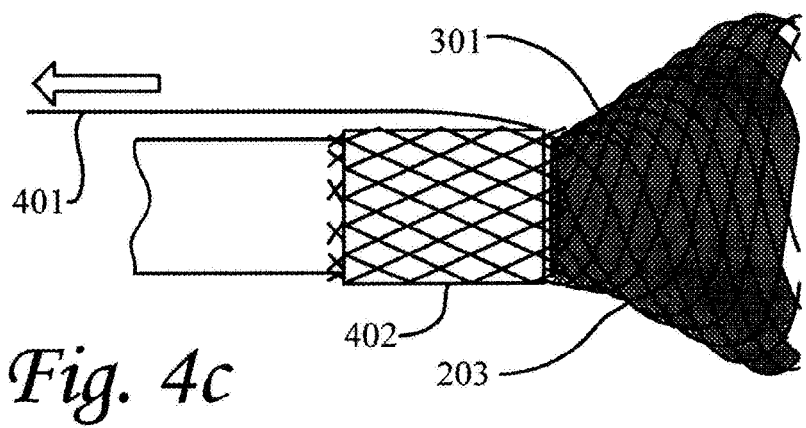

As previously mentioned, the deployment of the valve can be achieved in a variety of manners. As was described in FIGS. 2A-2B, the valve can be deployed by moving an outer catheter or sleeve that covers the valve. In that embodiment, the valve can be recaptured by the outer catheter or sleeve by moving the catheter or sleeve distally or the delivery catheter and valve proximally. In another embodiment, and as seen in FIGS. 4A-4C, the valve is released by irreversibly removing (unraveling) a knitted sleeve (weft knit) 402 that covers the valve 203 (shown with filter 301). More particularly, as seen in FIG. 4A, the valve 203 is attached to the distal end of the catheter 201. On top of the valve is a weft knit sleeve 402. A control thread 401 is attached to the weft knit and extends to the proximal end of the catheter. In one embodiment the unravelable knit is composed of polyester of a thickness between 10 µm and 60 µm. The knit can be a textile sheath that is held under tension. FIG. 4B shows the deployment of the valve by pulling on the control thread 401. In one embodiment, the thread 401 is connected to the distal end of the knit sleeve 402 and releases the valve by first removing material from the distal end of the sleeve 402. As the control thread 401 is pulled back and the sleeve is reduced in size, the distal end of the valve 203 having filter 301 is free to open. The weft knit sleeve 402 may be partially or fully removed to allow the physician control of the diameter or length of the valve. In FIG. 4C the weft knit is more fully removed enabling more of the length of the valve 203 and filter 301 to be free. In another embodiment the thread is attached to the middle or proximal end of the sleeve, and releases the valve by first removing material from the proximal end or from the middle of the sleeve.

Figure 5A:
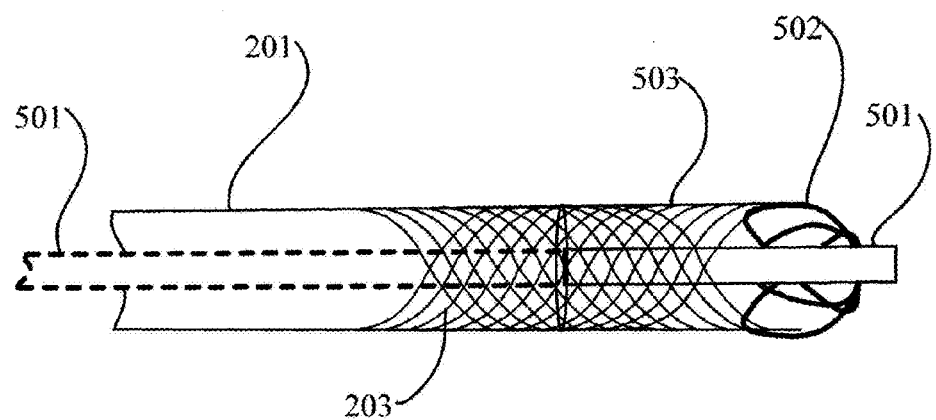
FIGS. 5A-5B are schematic diagrams showing an exemplary embodiment of a valve that can be deployed by movement of a guidewire.
Figure 5B:
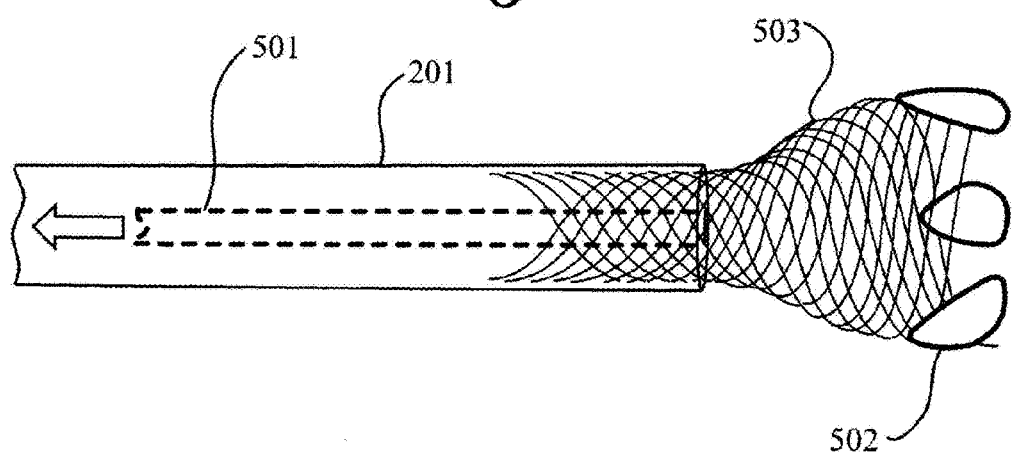

Turning now to FIGS. 5A and 5B, in another embodiment, a guidewire 501 can be used to deploy the valve 503. More particularly, valve 503 is provided with loops 502, which are attached at or near the distal end of the filaments of the valve 503. The loops 502 may be integral with the filaments or may be made of a separate material and attached to the filaments. As seen in FIG. 5A, the loops 502 are looped over the distal end of the guidewire 501 which extends through the lumen of the catheter 201. The loops at the end of the valve 502 are looped around the guidewire 501 while the catheter 201 and guidewire 501 are advanced through the vasculature. In this manner, the distal end of the valve is maintained in a closed position. When the guidewire 501 is withdrawn proximally as denoted by the arrow in FIG. 5B, the distal loops 502 are released, and the valve 503 is deployed.

Figure 6A:
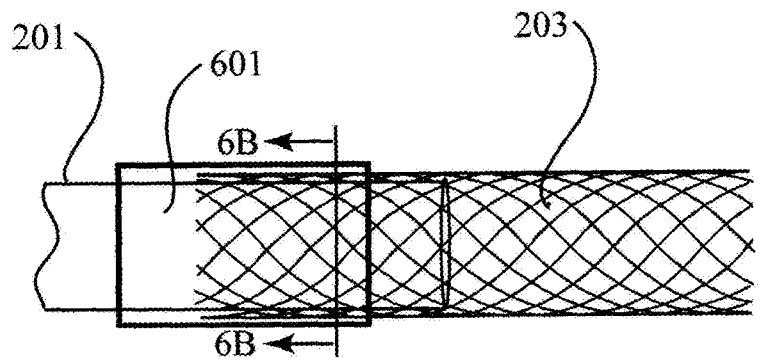
FIGS. 6A-6D show two exemplary methods of attaching the mesh component of the valve to a catheter.
Figure 6B:
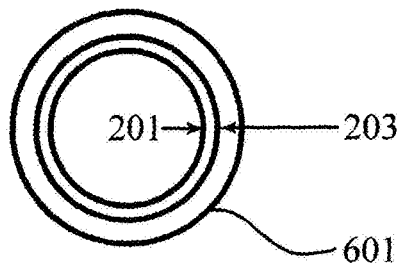

According to one aspect of the invention, the valve of any embodiment of the invention is attached to the distal end of the catheter in any of several manners. As seen in FIG. 6A, the valve 203 is attached to the catheter 201 by a sleeve 601 which overlies the proximal end of the valve 203 and extends proximal the proximal end of the valve 203 over the catheter 201. FIG. 6B shows a cross-sectional view of the catheter 201, valve 203, and sleeve 601. The sleeve 601 is bonded or mechanically held by a heat shrink process or other mechanical process to the catheter 201, and thus holds the distal end of the valve 203 on the catheter 201 by trapping the distal end of the valve between the catheter 201 and the sleeve 601.

Figure 6C:
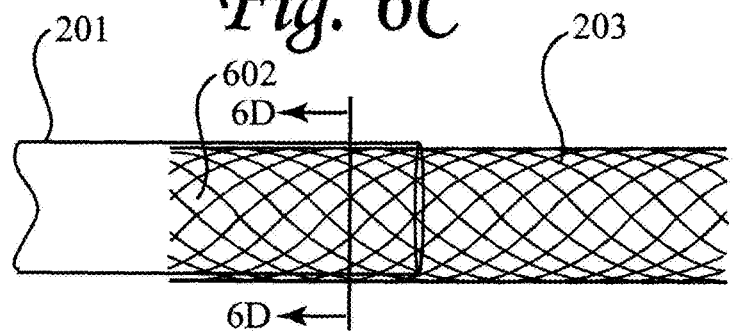
Figure 6D:
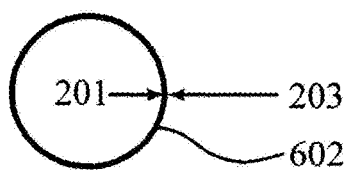

In one preferred embodiment, the valve is fused into the catheter. More particularly, as seen in FIG. 6C the valve 203 fused into the catheter 201 such that at the region 602 where the valve and catheter are fused, there is at most a minimal change to the inner or outer diameter of the catheter 201. FIG. 6D shows a cross-sectional view of the fused valve, where the catheter 201, valve 203 and fused region 602 are all of the same diameter. Fusion of the catheter and valve can be achieved by thermally melting the valve, melting the catheter, melting both the valve and the catheter, or by a chemical process.

Figure 7A:
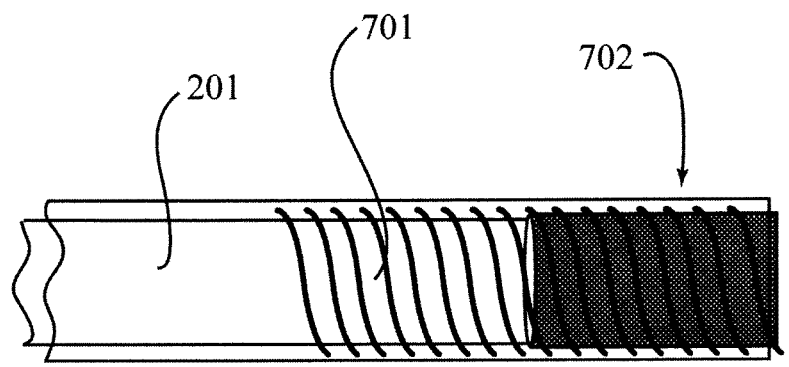
FIGS. 7A-7B show an exemplary embodiment of a valve composed of a single shape memory filament and a filter.
Figure 7B:
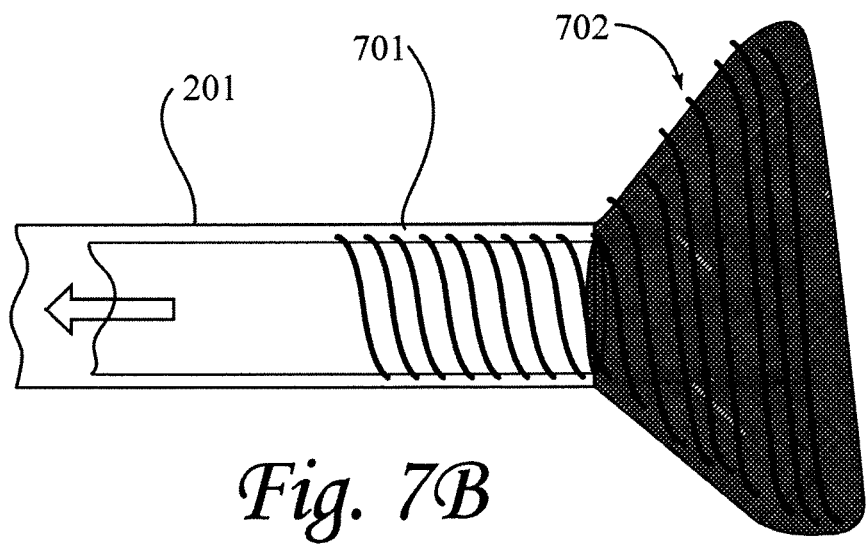

Turning now to FIGS. 7A and 7B, a valve 702 composed of a single filament coil is seen. The coil may be made of metal or polymer, and preferably the filament is a shape memory polymer. FIG. 7A shows a coil valve 701 in the retracted state on a catheter 201. The coil valve is provided with a filter 702 on its distal end. FIG. 7B shows the coil valve in the deployed state, where the valve 701 and the filter 702 are expanded at the distal end. Any of a variety of methods as previously disclosed can be used in deploying the valve.

Turning now to FIGS. 8A-8E, another embodiment of a deployment apparatus 800 is shown. The deployment apparatus 800 includes a delivery catheter 801, a valve 803, a deployment element 810, and a valve introducer 812. In distinction from certain prior embodiments, the delivery catheter is not required to be advanced relative to an outer catheter or outer sleeve to deploy the valve, as will become apparent from the following description.

The delivery catheter 801 is preferably a 3 French microcatheter or a 4 or 5 French catheter. The delivery catheter 801 is constructed of one, two or more than two layers. In one embodiment, the delivery catheter 801 includes an inner liner made of, e.g., FEP or PTFE, a central braid made of one or more of metal, polymer or liquid crystal polymer, and an outer polymeric cover made of, e.g., a polyether block amide thermoplastic elastomeric resin such as PEBAX®, polyetheretherketone (PEEK), or another suitable polymer.

The delivery catheter 801 has a distal end 805 provided with a valve seat 814 and a radiopaque marker band 816 located proximal to, distal of, or about the valve seat 814. The valve seat 814 is preferably defined by a circumferential inner groove located at the distal end 805 of the delivery catheter 801. The valve seat 814 may be defined directly on the delivery catheter, or be bonded or fused into the delivery catheter or to the distal end 805 of the delivery catheter. When the valve seat 814 is defined directly on the delivery catheter 801 and the delivery catheter is made from a multilayer construct, the valve seat 814 may be defined through one or two layers, or two layers and a partial depth of a third outer layer.

The valve 803 is generally as described in any of the embodiments above. The valve 803 may be a polymer braid coated with a polymer surface, a metal braid coated with a polymer surface, or a combination of polymer and metal braid coated with a polymer surface. The polymer surface may be a sheet, a sheet with holes drilled into it, or a mesh. The valve may be permeable or impermeable to blood. Regardless of the construct, the valve is a dynamic element that opens and closes based on local blood flow conditions. The proximal portion of the valve 803 includes mating structure 818 that can engage with the valve seat 812 at the distal end 805 of the delivery catheter 801 when the valve is advanced through the delivery catheter, as described in more detail below.

Figure 8B:
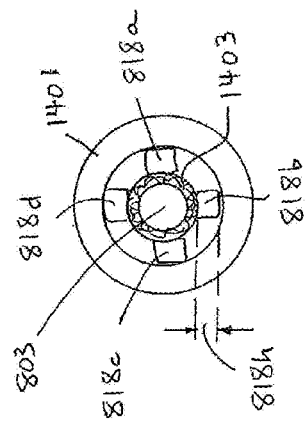
FIGS. 8A-8D show an embodiment of exemplary structure and method for attaching a valve to the delivery catheter, with FIGS. 8B and 8D being schematic cross-sections across lines 8B-8B in FIG. 8A and line 8D-8D in FIG. 8C, respectively.
Figure 8D:
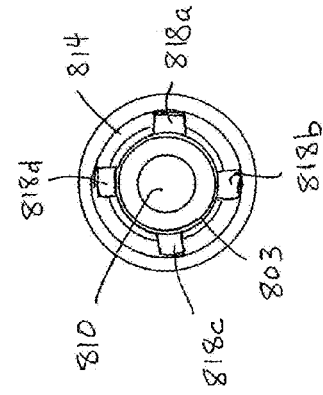
Figure 8A:
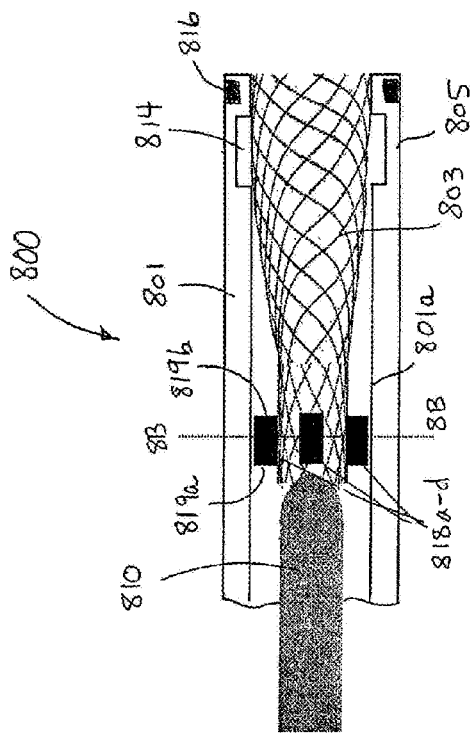
Figure 8C:
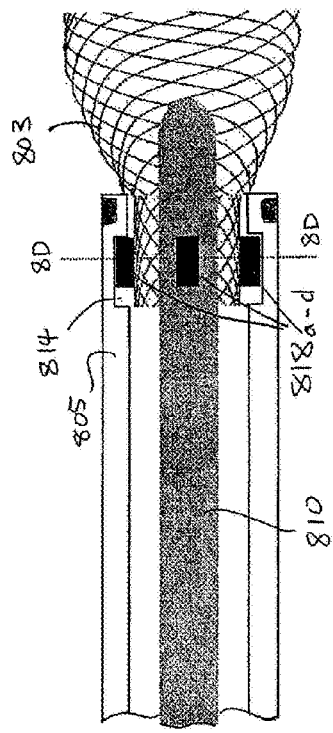

The mating structure 818 may include a shape memory polymer or elastic polymer that can be compressed for advancement through the body of the catheter, but which will automatically expand to seat in the valve seat 814. Referring to FIGS. 8C and 8D, when the mating structure 818 is engaged at the valve seat 814, such engagement locks the valve 803 relative to the delivery catheter 801 to prevent further distal movement of the valve relative to the delivery catheter and prevent the valve from exiting the distal end of the delivery catheter during the procedure. The mating structure 818 may be comprised of a plurality of independent features, e.g., four features, which each separately engage in the valve seat. Further, the features should be small in profile, e.g., not exceeding 0.25 mm in a radial 'height' dimension 818*h* through a center of the features, in order to maintain a low profile within the delivery catheter 801 as the valve 803 is advanced through the delivery catheter and also after the valve is engaged relative to the valve seat 814. By way of one example, the mating structure on the valve 803 includes a plurality of radiopaque metal slugs 818*a-d* bonded, fused, crimped or otherwise attached to the valve 803 and that can be received in the valve seat 814. The valve seat 814 may additionally include a radiopaque marker. In this manner, alignment of the valve with the valve seat can be visualized under fluoroscopy. The slugs 818*a-d* have proximal and distal surfaces 819*a*, 819*b* that are shaped to prevent the advancement or withdrawal of the valve 803 once the slugs are received in the valve seat. That is, the surfaces 819*a*, 819*b* may extend in planes perpendicular to the longitudinal axis of the delivery catheter. The proximal portion of the valve 803 is preferably constrained by the inner wall 801*a* of the delivery catheter 801 so as to define an inner diameter 803 through the valve.

The deployment element 810 is a push wire preferably generally similar in construction to a conventional guide wire. The outer diameter of the distal end 810*a* of the push wire is larger than the inner diameter of the proximal end of the valve 803. As a result, the push wire 810 can be used to provide a pushing force at the proximal portion 803*a* of the valve 803 and advance the valve through the delivery catheter 801; i.e., the distal end 810*a* of the push wire 810 and proximal portion 803*a* of the valve are relatively sized so that the push wire 810 will not freely extend through the valve 803. When the proximal portion 803*a* is constrained by inner wall 801*a*, the push wire 810 may include a polymer bead or metal bead to increase its distal end diameter and facilitate application of a pushing force on the valve. Additionally or alternatively, a cylindrical or tubular element may be fused or bonded onto the distal end of the push wire to aid in application of a pushing force against the valve. Additionally or alternatively, one or more metal or polymeric coils may be provided at the distal end of the push wire to increase its outer diameter. Any feature added to the distal end of the push wire should maintain trackability of the push wire. The push wire 810 is preferably made from a radiopaque material or contains one or more radiopaque markers, such as of platinum, along its length.

Figure 8E:
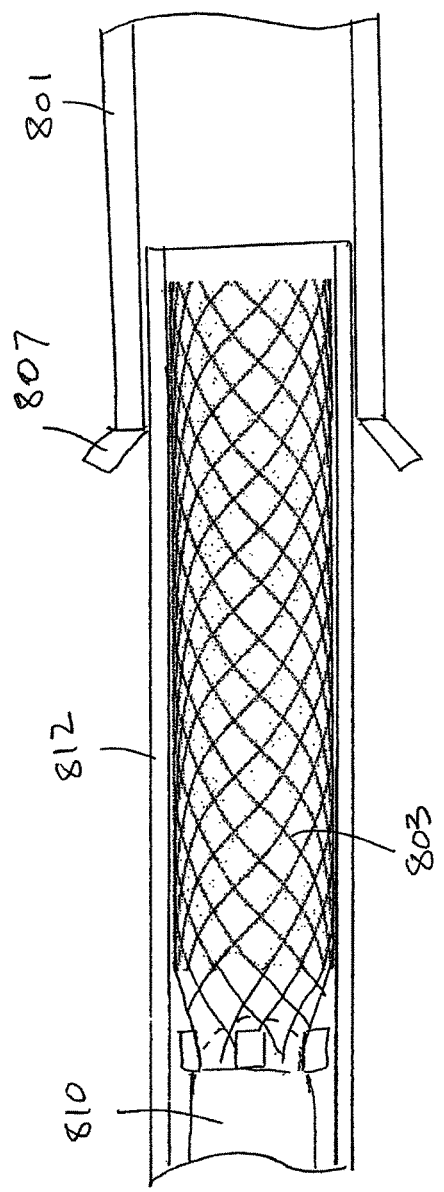
FIG. 8E is a schematic view of an introducer surrounding a valve and a push wire for introduction into the infusion port of a delivery catheter in accord with the embodiment shown in FIGS. 8A-8D.

The valve introducer 812 is a polymeric tube made, e.g., from PTFE. The introducer 812 is preferably 1 cm to 50 cm in length and may optionally be provided with a handle at its proximal end (not shown) to facilitate manipulation thereof. As shown in FIG. 8E, the valve 803 and preferably at least a portion of the push wire are held within the introducer 812, with the distal end of the valve 803 held in a collapsed configuration. The introducer 812, by retaining the valve 803 in the collapsed configuration, presents the valve in a size suitable for advancement through the delivery catheter 801. The introducer 812 has an inner diameter sufficiently large to contain the collapsed valve 803 and the push wire 810. The introducer 812 has an outer diameter smaller than the inner diameter of the infusion port 807 at the proximal end of the delivery catheter, so that the introducer can be advanced into the infusion port. In one embodiment, the inner diameter is 0.89 mm and the outer diameter is 0.96 mm.

Referring to FIGS. 8C and 8D, in use of the apparatus 800, a standard guidewire (not shown) is advanced through the vasculature of the patient ahead to a desired location of treatment. The delivery catheter 801 is advanced over the standard guidewire to the desired location. Once the delivery catheter 801 is at the desired location, the standard guidewire is removed from the delivery catheter and patient. The valve introducer 812 is then inserted into the infusion port of the delivery catheter 801. Depending on the length of the valve introducer 812, it may function as a guide for valve insertion solely at the proximal end of the delivery catheter or as a guide along a substantial length of the delivery catheter. The push wire 810 is then distally advanced relative to the introducer 812 to push the valve 803 (in an undeployed configuration) within the delivery catheter 801 toward the valve seat 814. When the valve 803 approaches the valve seat 814, the mating structure 818 automatically expands into and engages the valve seat 814 to lock the valve 803 relative to the distal end 805 of the delivery catheter 801. In the locked configuration, the valve is deployed at the distal end of the delivery catheter. The push wire 810 is then withdrawn from the delivery catheter 801.

Embolic agents are then infused through the delivery catheter 801 and the valve 803. The valve 803 functions as described above. That is, as the embolic agents are infused, the valve 803 enables forward flow but prevents reverse flow (reflux) of embolic agents in the blood vessel in which the delivery catheter is inserted. As a result of not using a tube within a tube construct during infusion of embolic agents (i.e., a delivery catheter with an outer sleeve), as described in various above embodiments, a larger delivery catheter can be used to provide greater flow of embolic agents to the treatment site. After infusion is complete, the delivery catheter 801, along with the valve 803 at its distal end 805, is retracted from the patient.

It is also appreciated that while positive engagement between a valve and valve seat is desired, it is not necessary. That is, provided alignment of the valve relative to the distal end of the catheter can be fluoroscopically visualized, such as with the use of respective radiopaque markers, the valve can be manually retained at the appropriate location relative to the catheter.

Another embodiment similar to deployment apparatus 800 includes a deployment element constructed of a thin wire attached to the valve. The wire preferably has a diameter of 0.025 mm to 0.125 mm, and may be a standard wire or a flattened wire. A flattened wire may more closely correspond to the inner surface of the catheter to limit any obstruction of the lumen of the catheter. In use, the thin wire advances the valve to the valve seat and then remains attached to the valve and within the catheter during infusion of the embolic agent.

Figure 9A:
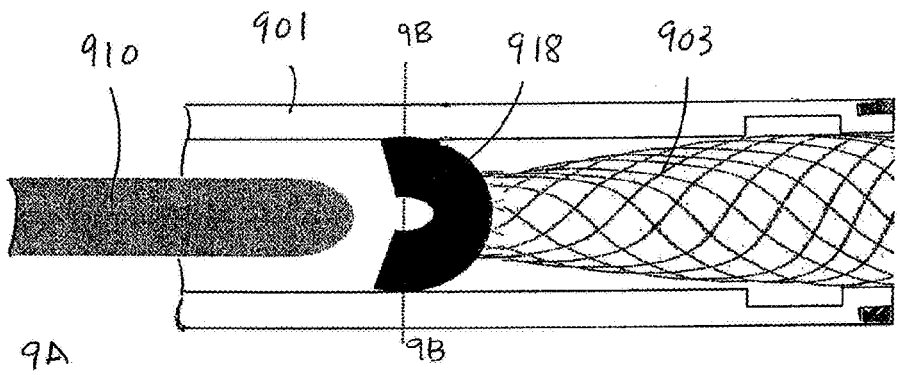
FIGS. 9A-9D show another embodiment of exemplary structure and method for attaching a valve to the delivery catheter, with FIGS. 9B and 9D being cross-sections across line 9B-9B in FIG. 9A and line 9D-9D in FIG. 9C, respectively.
Figure 9B:
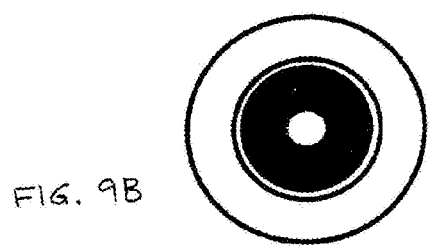
Figure 9C:
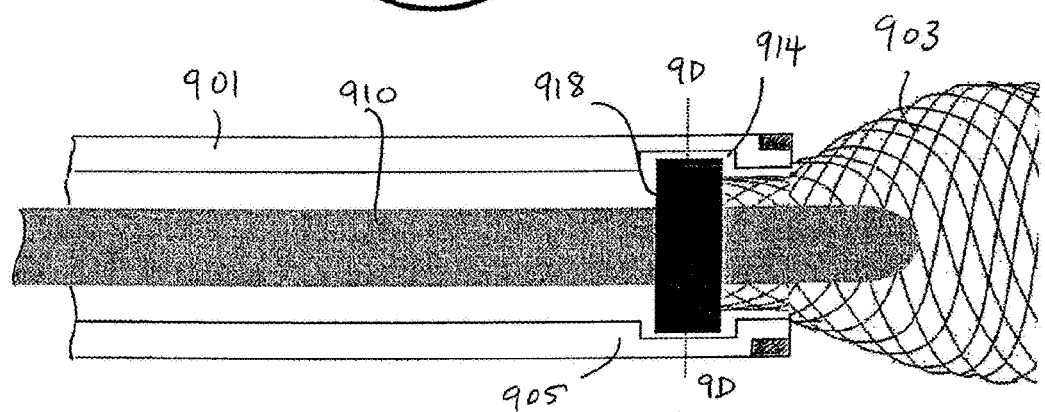
Figure 9D:
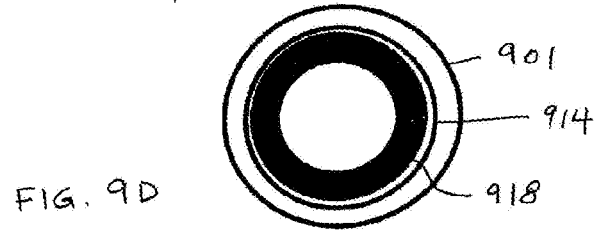

Turning now to FIGS. 9A-9D, another embodiment of a deployment apparatus 900 is shown. The deployment apparatus 900 is substantially similar to apparatus 800 and includes a delivery catheter 901, a valve 903, a push wire 910 and a valve introducer (as described with respect to introducer 812). The difference between apparatus 900 and prior described apparatus 800 is the mating structure 918 provided to the valve to lock the valve relative to the valve seat. In FIGS. 9A and 9B the mating structure 918 is a proximal ring-shaped flange that is radially compressed or otherwise deformed to a size permitting advancement through the delivery catheter as its is pushed by the push wire 910. As shown in FIGS. 9C and 9D, once the push wire 910 delivers the valve 903 to the distal end 905 of the delivery catheter 901, the flange 918 expands into the valve seat 914 once located at the valve seat to lock the valve 903 relative to the valve seat 914. The ring-shaped flange 918 may be defined by an elastic element coupled to the braid of the valve or a metal braid or metal stent portion of the valve that has a much higher expansion force than a remainder of the valve.

Figure 10A:
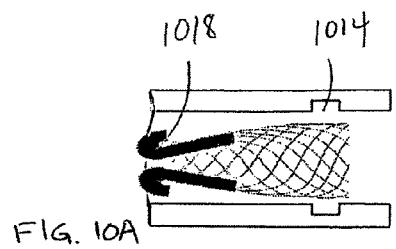
FIGS. 10A-13B show additional exemplary structures and methods for attaching a valve to the delivery catheter, with the 'A' and 'B' figures corresponding to the valve being located in pre-seated position and a post-seated position, respectively, relative to a valve seat of the delivery catheter.
Figure 10B:
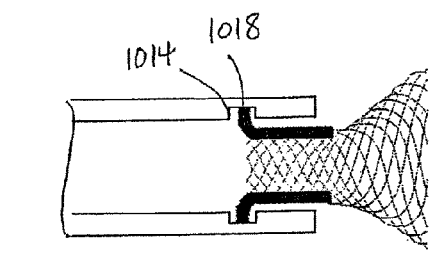
Figure 11A:
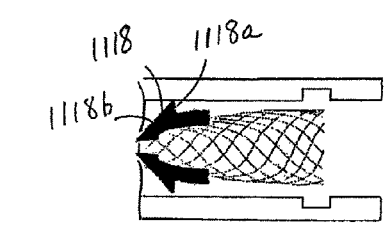
Figure 11B:
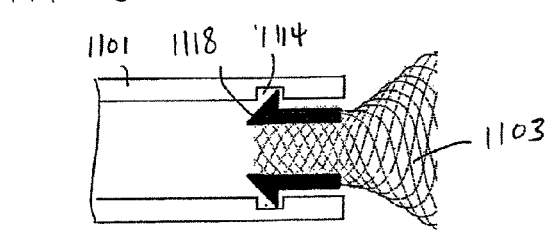
Figure 12A:
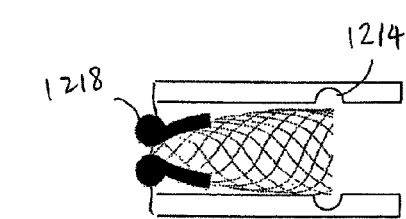
Figure 12B:
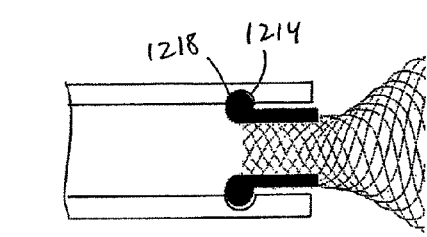
Figure 13A:
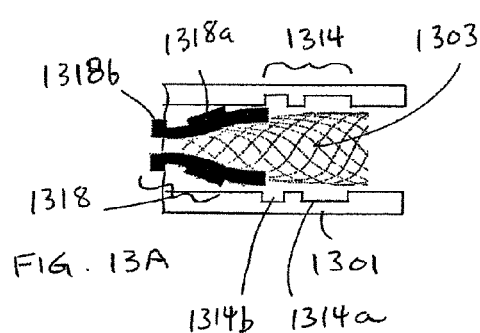
Figure 13B:
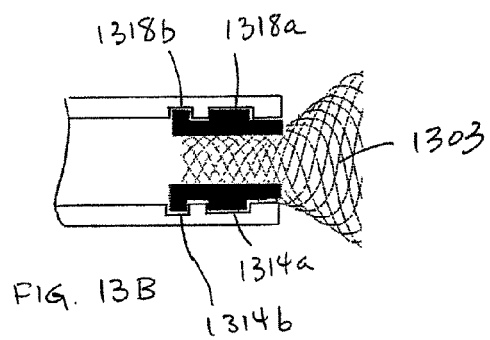

FIGS. 10A-12B illustrate additional embodiments of a flange mating structure that can be used on the valve for locking engagement between a valve and a valve seat. FIGS. 10A and 10B show a flange 1018 having a proximal end which in cross-section appears L-shaped or J-shaped and that engages within the valve seat 1014. FIGS. 11A and 11B show a flange 1118 having an abutting front surface 1118a and a rear bevel 1118b (appearing as a barb in cross-section) such that the flange has a proximal taper (i.e., a smaller proximal diameter and a relatively larger distal diameter). This structure facilitates proximal release of the flange 1118 from the valve seat 1014 for removal of the valve 1103 from the delivery catheter 1101, particularly suitable in conjunction with an embodiment of the apparatus provided with a valve retraction element, discussed further below. FIGS. 12A and 12B show a flange 1218 comprised of an o-ring, and wherein the valve seat 1214 is in the form of a circular channel in which the o-ring is captured. FIGS. 13A and 13B illustrate another embodiment of a valve seat 1314 at the distal end of the delivery catheter 1301 and corresponding mating structure 1318 on a valve 1303. The valve seat 1314 and mating structures 1318 are 'keyed' with multiple longitudinally displaced structures that enhance engagement between the valve 1303 and the valve seat 1314, but that prevent locking engagement until the structures are in proper longitudinal alignment with each other. By way of the example shown, the valve seat may include a plurality of longitudinally displaced channels 1314a, 1314b, wherein a distal channel 1314a has a greater width than a proximal channel 1314b. The mating structure 1318 includes a distal flange 1318a sized to be received in the distal channel 1314a but too large to be received in the proximal channel 1314b. The mating structure also includes a proximal flange 1318b that is appropriately sized for being received and captured by the proximal channel 1314b. When the proximal and distal flanges 1318a, 1318b are aligned with the proximal and distal channels 1314a, 1314b, the flanges expand into the respective channels and lockingly engage the valve 1303 relative to the distal end of the delivery catheter 1301. In any of the embodiments described above, the flange may include a circumferentially uninterrupted element or be comprised of separate elements radially displaced about the proximal portion of the valve. Furthermore, while the valve seat is shown as comprising 'negative' space and the mating structure as one or more elements that expand into such space, it is appreciated that the structure for the valve seat and mating structure may be reversed; i.e., such that the valve seat comprises elements that extend into the lumen of the delivery catheter and the mating structure being a groove or other negative space about the proximal end of the valve. However, such a reverse configuration is less desired as it reduces the diameter of the infusion path at the distal end of the delivery catheter.

Figure 14B:
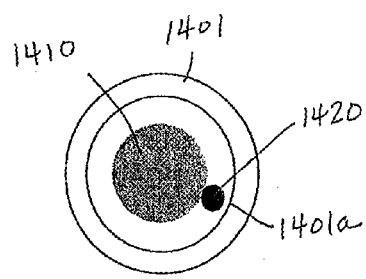
FIGS. 14A-17B show embodiments with exemplary structure for releasing the valve from the delivery catheter so that the valve may be withdrawn into the delivery catheter, with the 'A' and 'B' figures corresponding to longitudinal section and cross-section views, respectively.
Figure 14A:
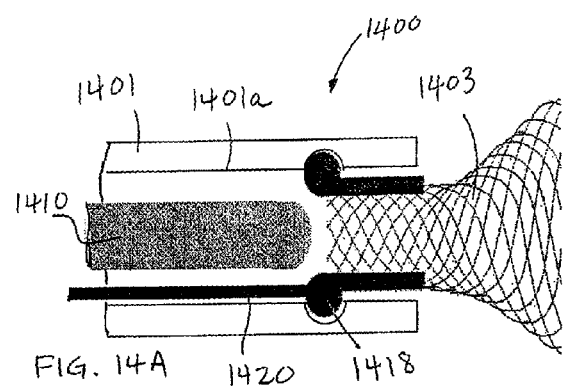

Turning now to FIGS. 14A and 14B, another embodiment of a deployment apparatus 1400 is shown. The deployment apparatus 1400, which includes similar elements to apparatus 800, has a delivery catheter 1401, a valve 1403, a push wire 1410 and a valve introducer (as described with respect to introducer 812). In addition, the apparatus 1400 includes a refraction element 1420 that is attached to the proximal portion of the valve 1403, and more preferably to the mating structure 1418 thereof, to apply a release and retraction force to the valve to thereby disengage the valve from the valve seat and withdraw the valve through the delivery catheter.

The retraction element 1420 is a pull wire attached to the mating structure 1418. The pull wire 1420 may be flattened or otherwise formed such that it conforms close to the inner surface 1401a of the delivery catheter 1401 to maximize the usable space within the lumen of the delivery catheter for delivery of the embolic agent. The pull wire 1420 should have sufficient mechanical strength in tension to release and withdraw the valve 1403 from the delivery catheter. However, it is appreciated that the pull wire 1420 is not required to have high compressive stiffness, as the push wire 1410 extends parallel to the pull wire 1420 and performs the function of advancing the valve to the distal end of the delivery catheter.

Use of the apparatus is similar to apparatus 800. The valve 1403, push wire 1410 and pull wire 1420 are all surrounded with an introducer (not shown) that facilitates introduction of such elements into the infusion port of the delivery catheter. The push wire 1410 advances the valve 1403 and pull wire 1420 out of the introducer and to the distal end of the delivery catheter 1401. Once the valve 1403 engages the valve seat 1414, the push wire 1410 is withdrawn from the delivery catheter 1401. Embolic agents are then infused through the delivery catheter 1401 to treat the patient. After the embolic agents have been infused, the valve 1403 can be withdrawn into the delivery catheter 1401 by applying a sufficient tensile force on the pull wire 1420 to release the valve 1403 from the valve seat 1414 and retract it into the delivery catheter 1401. The delivery catheter is then removed from the patient. Optionally, the pull wire 1420 may be used to completely withdraw the valve 1403 from the delivery catheter 1401 prior to removing the delivery catheter from the patient.

Figure 15B:
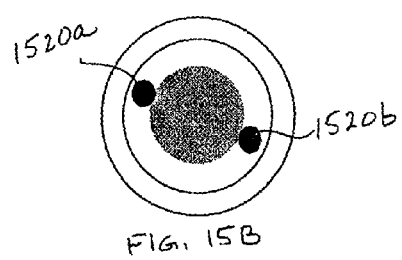
Figure 15A:
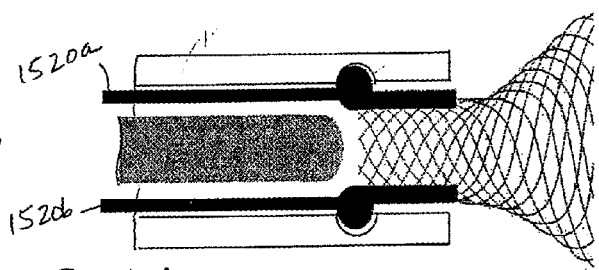
Figure 16B:
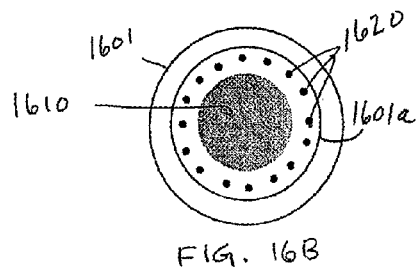
Figure 16A:
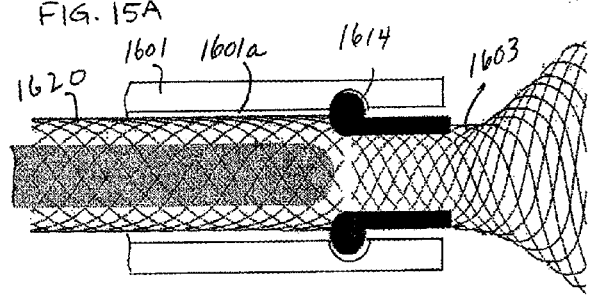
Figure 17B:
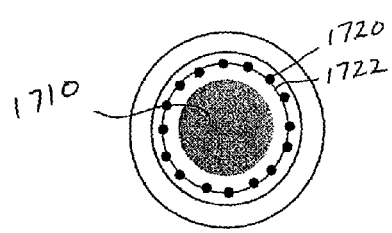
Figure 17A:
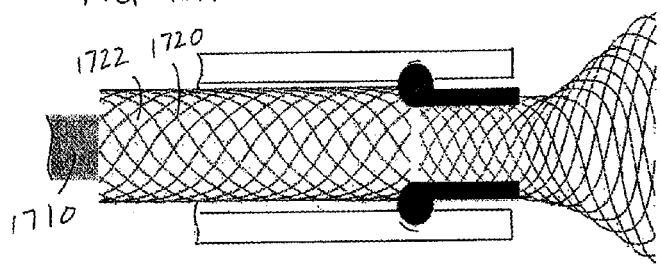

In addition to a single pull wire, the retraction element may take other forms which may be similarly used to withdraw the valve from the delivery catheter after infusion of the embolic agent. For example, referring to FIGS. 15A and 15B, the retraction element includes a plurality of pull wires, such as the pair of pull wires 1520a, 1520b shown. In addition, referring to FIGS. 16A and 16B, the retraction element may comprise a tubular retraction braid 1620 of multiple metal wires or polymeric filaments. The braid 1620 may be made from stainless steel, Elgiloy®, Nitinol or another elastic material. The tubular braid 1620 may have a predefined diameter that is the same or larger than the diameter of the lumen of the delivery catheter. In this manner the refraction braid can be held taut against the pushing force of the push wire 1610 in order to decrease it to a diameter smaller than the diameter of the lumen of the delivery catheter 1601. Once the push wire 1610 advances the valve 1603 to the valve seat 1614, the tension is released from the braid 1620 to permit the braid to be held outward against the inner wall 1601a of the delivery catheter 1601. Further, referring to FIGS. 17A and 17B, a retraction braid 1720 may be coated with a polymeric coating 1722. The polymeric coating 1722 may include, e.g., one or more of polyurethane, polyamide, polyimide, PTFE or FEP such that the refraction element defines a catheter body. It is noted that in embodiments using a retraction element separate from a push wire, the retraction element can be designed with a low compressive strength, as the separate push wire 1710 performs advancement of both the valve and the retraction element through the delivery catheter.

As yet another alternative, the push wire and retraction element may be comprised of a single element having sufficient compressive and tensile strengths to advance the valve to the valve seat and retract the valve from the valve seat at the conclusion of the procedure. Such single element should be of a design which retains usable space within the lumen of the delivery catheter to permit sufficient infusion of embolic agents.

Figure 18A:
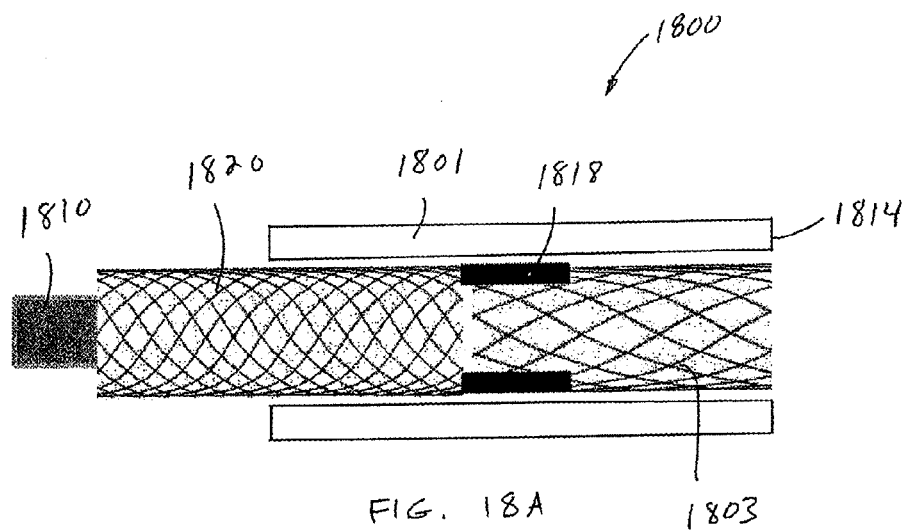
FIGS. 18A and 18B show another embodiment of exemplary structure and method for attaching a valve to the delivery catheter.
Figure 18B:
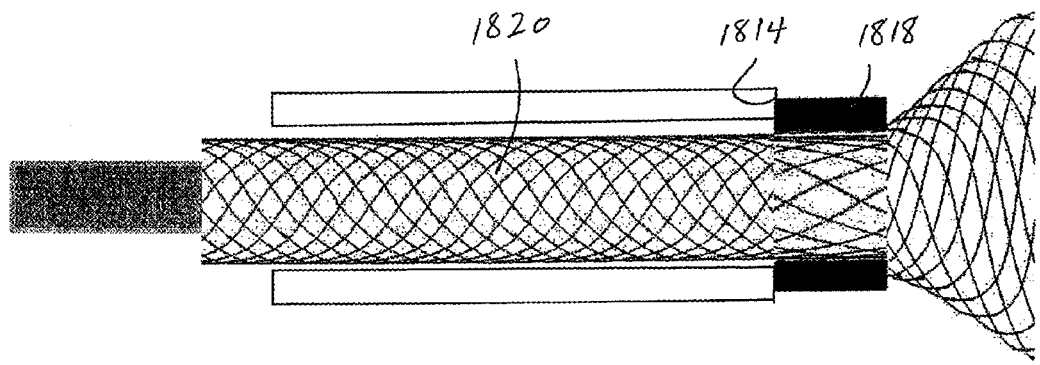

Referring to FIG. 18A, another deployment apparatus 1800 is shown. The deployment apparatus 1800 has a delivery catheter 1801, a valve 1803, a push wire 1810, a retraction element in the form of a polymer-coated braid 1820, and a valve introducer (as described with respect to introducer 812). The valve seat 1814 is defined by the distal end of the delivery catheter 1801. The mating structure 1818 of the valve seat 1814 is compressed for advancement through the delivery catheter. As shown in FIG. 18B, once the mating structure 1818 passes through the distal end 1805 of the delivery catheter 1801, the mating structure expands into contact with the valve seat 1814. The retraction element 1820 maintains tensile force on the valve 1803 to hold the valve 1803 against the valve seat 1814.

In another embodiment of the invention, no deployment element is required. The valve is advanced through the catheter to a valve seat using hydraulic pressure. Any of the valve designs described above with respect to FIGS. 8-17 are provided within the catheter, e.g., using an introducer. Then, via the infusion port, a bolus of saline or heparinized saline is injected into the catheter behind the valve to force the valve to the distal end. U.S. Pat. No. 6,306,074, which is incorporated by reference herein, describes the use of hydraulic pressure to advance treating elements such as radioactive therapeutic seeds through a catheter to a delivery location. Hydraulic pressure can similarly be applied to advance the valve, taking into account frictional forces between the valve and inner surface of the catheter, blood pressure and gravitational force. It is appreciated that when the valve is within the catheter, it is sufficiently radially collapsed to provide an adequate barrier within the catheter on which the bolus of solution acts.

Figure 19:
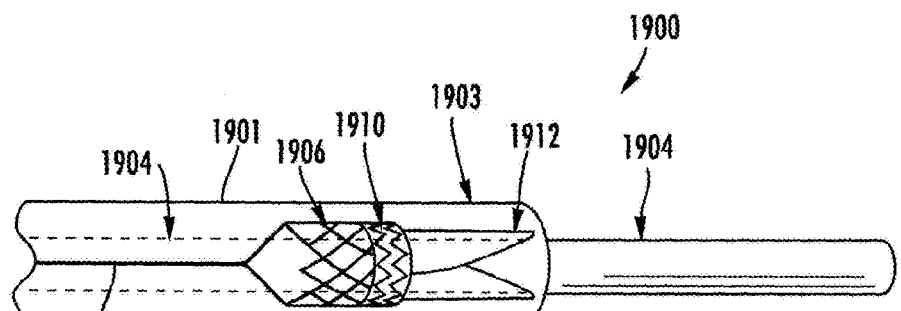
FIG. 19 is a schematic view of the distal end of another embodiment of an apparatus for delivering a valve at the distal end of a delivery catheter.
Figure 20:
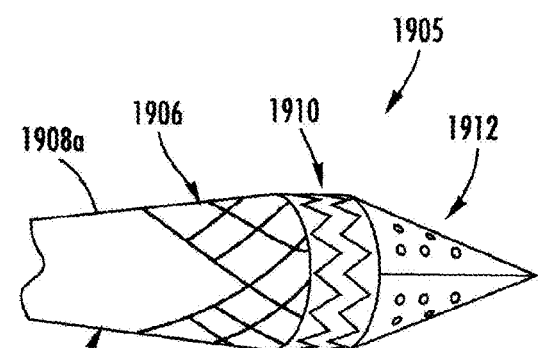
FIG. 20 is a schematic view of the valve of FIG. 19.
Figure 21A:
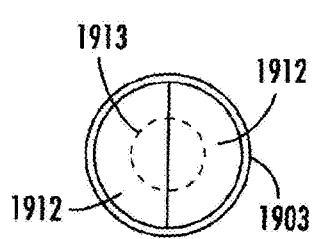
FIGS. 21A-21C are distal end views of respective embodiments employing different valve structure for the valve of FIG. 20.
Figure 21B:
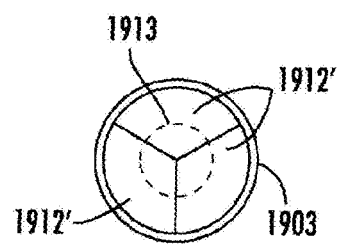
Figure 21C:
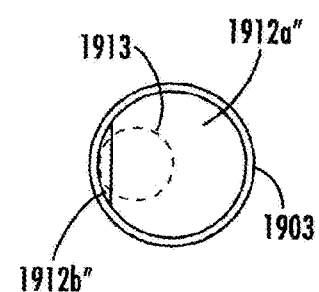
Figure 22:
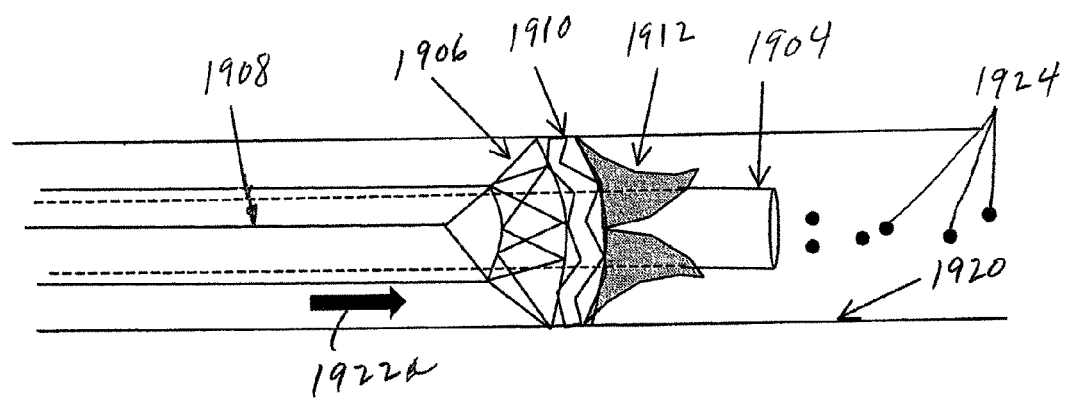
FIGS. 22-23 illustrate the apparatus of FIG. 19 in deployed configurations.
Figure 23:
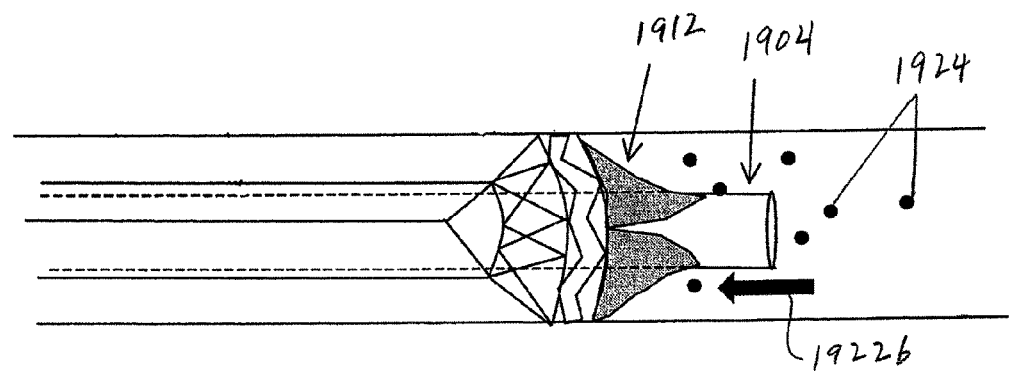

Another embodiment of a delivery apparatus 1900 is shown at FIG. 19. The delivery apparatus 1900 includes an outer catheter 1901 having a proximal end (not shown) and a distal end 1903, an inner catheter 1904 extendable through the outer catheter, and a valve 1905 situated in the distal end 1903 of the outer catheter 1901. The valve 1905 includes a proximal expandable framework 1906, one or more control members 1908 (or 1908a, 1908b in FIG. 20) coupled to the proximal end of the framework 1906, a central collar 1910 at the distal end of the framework 1906, and one or more valve flaps 1912 extending distally from the collar 1910. The framework 1906 and collar 1910 are preferably made from form an expandable structure. Both the framework 1906 and collar 1910 are preferably made of a material have shape memory or other spring-like expansible properties so that they are self-expanding, or are constructed of a non-shape memory or non-springy material that can be expanded under force, e.g., by balloon expansion as described further below. The framework 1906 and collar 1910 may be a mesh of metal wire or polymeric filaments, a wire or tubular stent structure, or other suitable structure. The framework 1906 and collar 1910 may be integrally formed together, or separately formed and then coupled together. The collar 1910 is sufficiently expansible and appropriately sized to contact the inner wall of an artery when partially or fully expanded. The valve flaps 1912 are preferably constructed in a manner similar to above described valve structures. For example, the valve flaps 1912 may each comprise a filamentary structure or other mesh overlaid with a polymer coating. The valve flaps may be structured to permit blood and/or contrast agent to pass through the material thereof, or may be impermeable to such fluids. The valve flaps 1912 may include two flaps 1912 of equal size in a duck-bill formation (FIG. 21A), three or more flaps 1912' of equal dimension (FIG. 21B), or flaps 1912a", 1912b" of different size (FIG. 21C). In each embodiment, distal portions of the flaps may be shaped (as shown by broken lines) to together define a circular opening 1913 for passage of the inner catheter 1904 therethrough. The control member 1908 may advance and retract the valve 1905 relative to the outer and inner catheters 1901, 1904 between housed and deployed configurations. Alternatively, the valve 1905 can be coupled directly to the inner catheter 1904, with movement of the inner catheter relative to the outer catheter 1901 effecting movement of the valve 1905 between a housed configuration and a deployed configuration. In a first housed configuration, the framework 1906 and collar 1910 are radially constrained by the outer catheter 1901, and the flaps 1912 are held closed against each other (prior to insertion of the inner catheter 1904 through the valve) (FIGS. 21A-21C). In a second housed configuration shown in FIG. 19, the framework 1906, collar 1910, and valve 1905 remain radially constrained within the outer catheter 1901, and the inner catheter 1904 is extended through the valve flaps 1912. In a first deployed configuration, operation of the control member 1908 distally advances the valve 1905 out of the distal end of the outer catheter 1901, and the collar 1910 is permitted to self-expand until the proximal ends of the valve flaps 1912 are adjacent the arterial wall 1920 (FIG. 22). Alternatively, where the valve 1905 is coupled relative to the inner catheter 1904, the inner catheter functions as the control member and the inner catheter and outer catheter are moved relative to each other to advance the valve out of the distal end of the outer catheter into the same deployed configuration. In the first deployed configuration, the valve 1905 is fluid opening is opened by downstream fluid pressure 1922a on the proximal side of the valve. The embolizing agent 1924 is infused through the inner catheter 1904. When the fluid pressure changes such that higher pressure 1922b is located on the distal side of the valve, such as may occur during a change in blood pressure or by user-operation upon infusion of an embolic agent 1924, the valve 1905 dynamically changes due to the changes in pressure conditions to a second deployed configuration in which the distal end of the valve flaps 1912 close against the inner catheter 1904 (FIG. 23). This prevents any embolizing agent from passing back beyond the valve.

Figure 24:
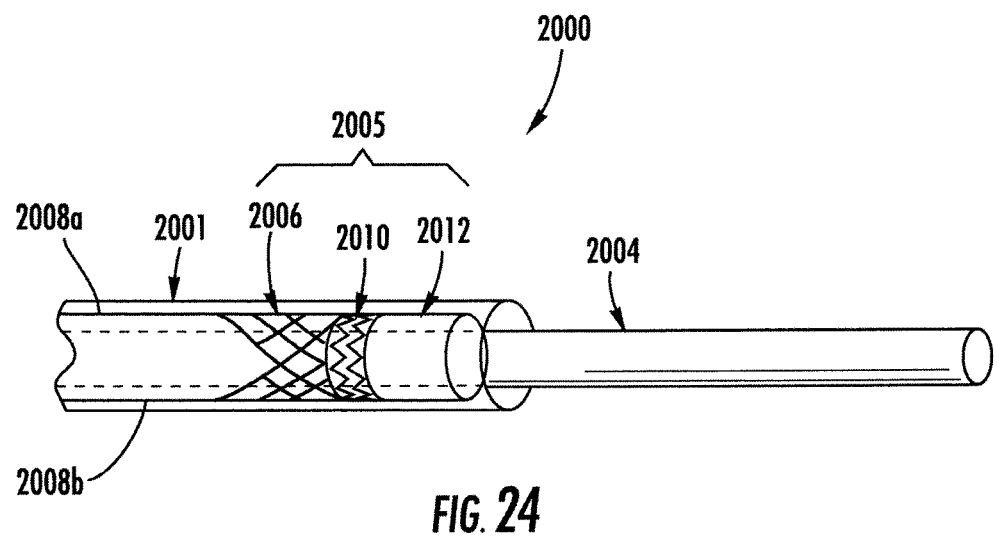
FIGS. 24-26 are schematic views of another apparatus for deployment of a sleeve valve, with FIG. 24 showing the valve in a housed configuration and FIGS. 25 and 26 showing the valve in two different deployed configurations.
Figure 25:
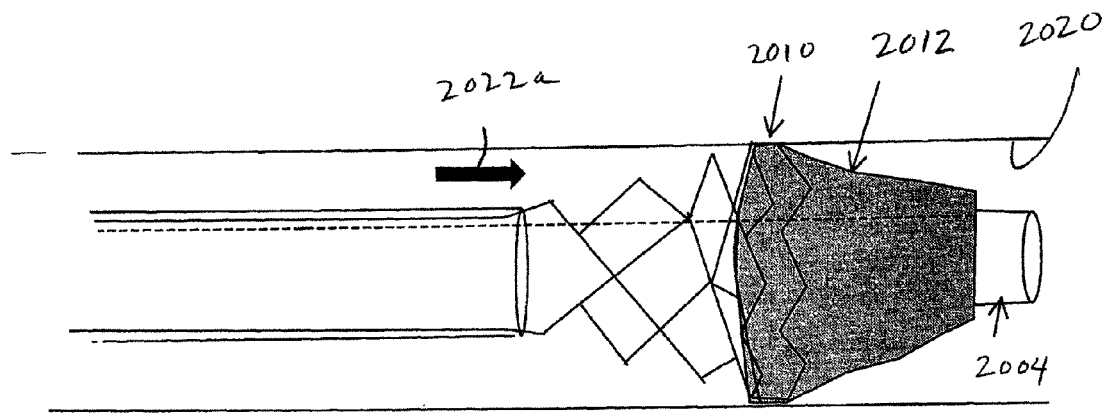
Figure 26:
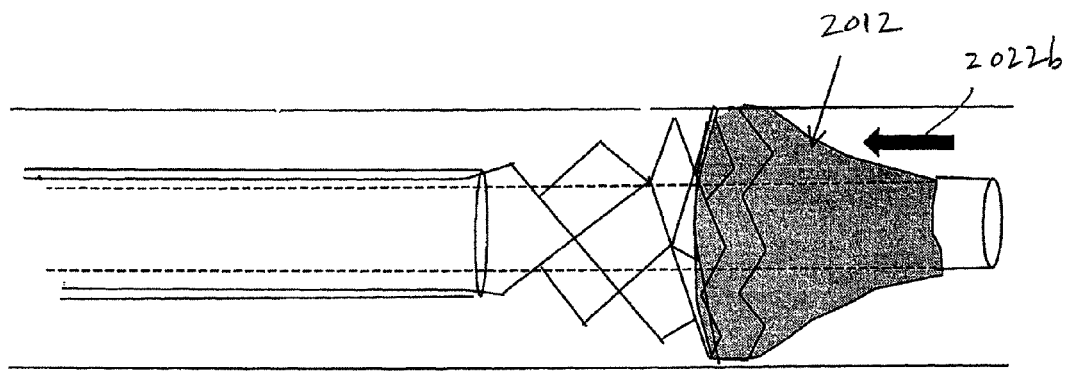

Turning now to FIG. 24, another embodiment of a delivery apparatus 2000, substantially similar to delivery apparatus 1900, is provided with a valve 2005. The valve 2005 includes a proximal expandable framework 2006, optionally one or more control members 2008a, 2008b coupled to the proximal end of the framework 2006, a central collar 2010 at the distal end of the framework 2006, and a tubular valve sleeve 2012. The sleeve 2012 is preferably constructed in a manner similar to any above described valve, e.g., with a polymer-coated filamentary construct, but may be of other construction. In a housed configuration, the sleeve 2012 resides between the outer catheter 2001 and inner catheter 2004 of the delivery apparatus 2000, with the inner catheter 2004 extending through the sleeve. The sleeve 2012 may be advanced relative to the outer catheter 2001 into a deployed configuration by mounting it relative to the inner catheter 2004 and advancing the inner catheter relative to the outer catheter, or alternatively by operation of the control members 2008a, 2008b to move the sleeve relative to both the outer catheter 2001 and the inner catheter 2004. Regardless of how the collar 2010 of the valve 2005 is freed of the outer catheter, once freed the collar 2010 expands to contact the arterial wall 2020 and deploy the valve 2012. In a first pressure condition 2022a in which a higher pressure is located upstream of the valve sleeve 2012, the blood may flow between the valve and the inner catheter (FIG. 25). In a second deployed configuration, resulting when the pressure 2022a within the blood vessel 2020 changes to define a higher pressure condition downstream of the valve sleeve 2102, the valve sleeve 2012 closes against the inner catheter 2004 (FIG. 26).

Figure 27:
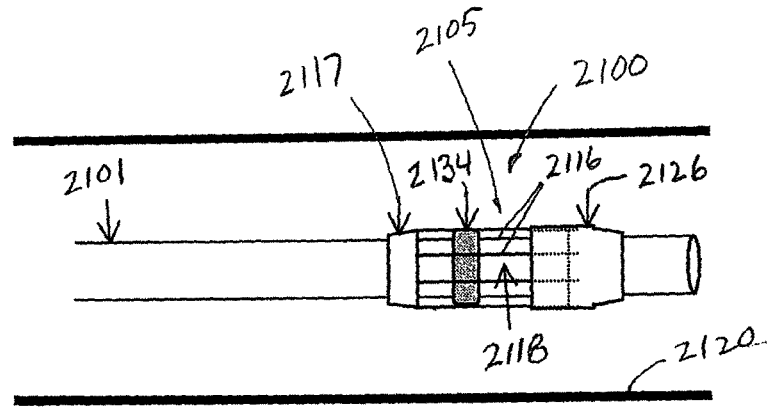
FIGS. 27-29 are schematic views of an apparatus for deployment of a valve that uses a balloon, with FIG. 27 showing the valve in a closed configuration and FIGS. 28 and 29 showing the valve in two different deployed configurations.
Figure 28:
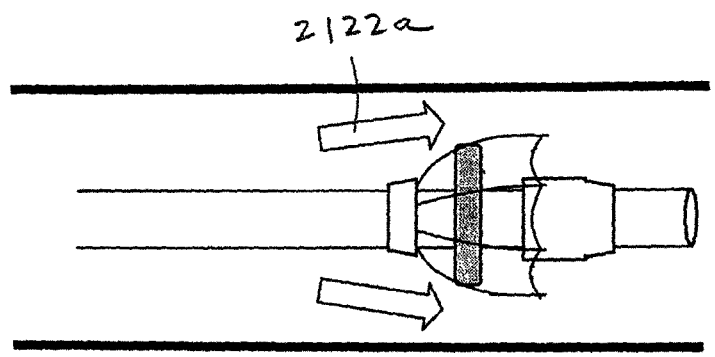
Figure 29:
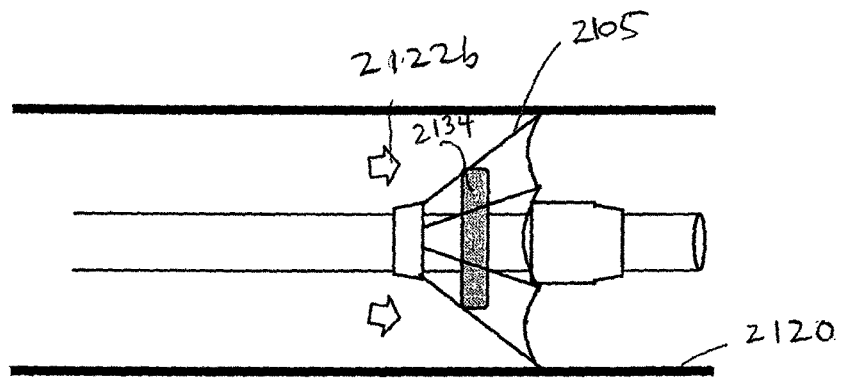

Turning now to FIG. 27, another embodiment of a delivery apparatus 2100 is shown. The delivery apparatus 2100 includes a valve 2105 coupled to a catheter 2101. The valve 2105 includes a plurality of struts 2116 coupled at their proximal ends by a collar 2117. A suitable filter material 2118 extends between the struts 2116. The delivery apparatus 2100 also includes a guard 2126 coupled to the catheter 2101 that shields the arterial wall 2120 from the distal ends of the struts 2116 when the valve 2105 is in a non-deployed configuration. The delivery apparatus 2100 includes a control member in the form of a balloon 2124 that, when expanded, applies a radial force to the struts that sufficiently flexes the struts to release the valve from the guard 2126. This results in the valve 2105 entering a deployed configuration. The balloon 2124 may be expanded via use of a dedicated lumen of the inner catheter 2104, a distinct inflation catheter or via any other suitable system (such as that described below with respect to FIGS. 30-32). In the deployed configuration, when a higher fluid pressure condition 2122a is located upstream of the valve, forward flow of blood is permitted about the exterior of the valve (FIG. 28). However, when an embolic agent is infused, e.g., at relatively high pressure, a higher fluid pressure condition is defined downstream of the valve, and the valve 2105 dynamically and rapidly responds to the changing flow conditions and fully opens to the arterial wall 2120 preventing flow of embolizing agent past the valve (FIG. 29).

Figure 30:
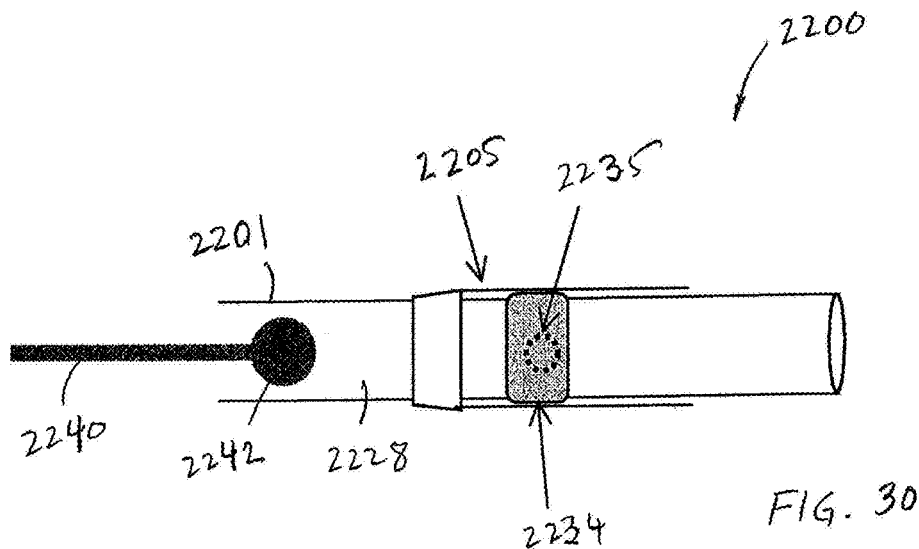
FIGS. 30-32 are schematic view of another apparatus for deployment of a filter that uses a balloon.
Figure 31:
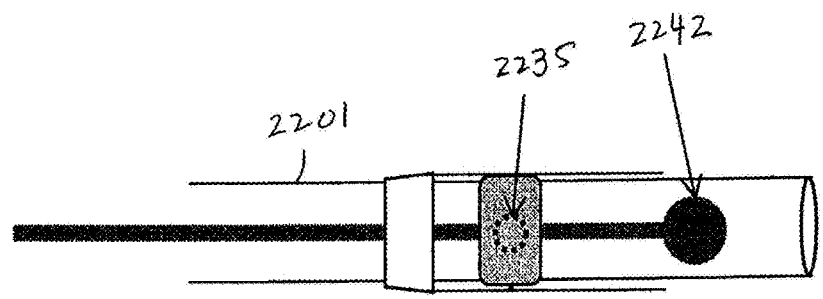
Figure 32:
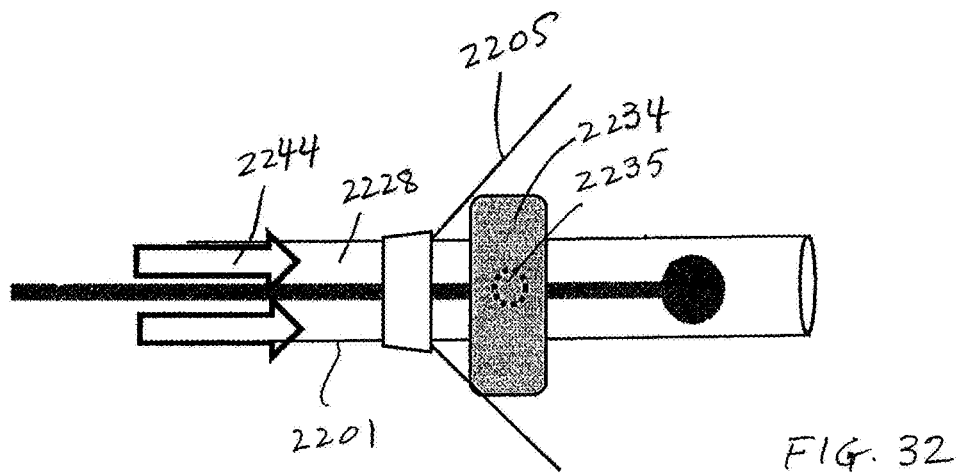

Turning now to FIGS. 30 to 32, another embodiment of a delivery apparatus 2200 is shown. A catheter 2201 includes an outer control member balloon 2234. A valve 2205 is provided over the balloon 2234 and includes filtering material 2212 extending across circumferentially displaced struts 2216. The balloon is positioned radially centered between the struts. The balloon 2224 includes a pressure valve 2235 in communication with the lumen 2228 of the catheter 2201. A guidewire 2240 provided with an occlusive tip 2242 is advanced through the lumen 2228 of the catheter 2201. The occlusive tip 2242 is advanced past the pressure valve 2235 (FIG. 31). An injectate 2234, such as saline, is then injected into the catheter lumen 2228. Referring to FIG. 32, sufficient fluid and pressure are provided to cause the injectate to enter the pressure valve 2235 and fill the balloon 2234. The balloon 2234 fills to high pressure and then seals to prevent leakage to low pressure conditions. As the balloon 2234 fills to a high pressure state, it contacts the valve 2205 to move the valve to a deployed configuration. The guidewire 2240 may then be withdrawn from the catheter 2201. The valve is then used as described above in conjunction with the infusion of an embolizing agent through the catheter 2201. After completion of the procedure, the catheter 2201 can be drawn back into an outer catheter (not shown) and such that contact between the valve 2205 and the distal end of the outer catheter will overcome the pressure valve 2235 and cause the pressure valve to release, the balloon 2234 to deflate and the valve to re-assume a non-deployed configuration for withdrawal from the patient.

Figure 33:
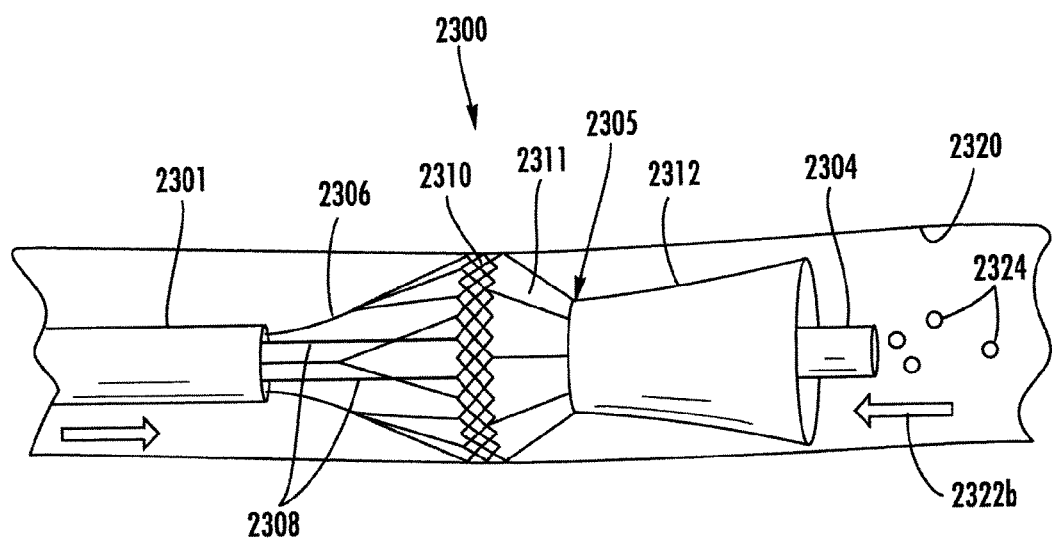
FIG. 33 is a schematic view of another apparatus for deployment of a valve.

Referring now to FIG. 33, another embodiment of a delivery apparatus 2300 is shown. The apparatus includes an outer catheter 2301, an inner catheter 2304 extending through the outer catheter, and valve 2305 comprising an expandable wire framework 2306 coupled to the inner catheter 2304 or operable via independent control members 2308, an expandable collar 2310 coupled to the framework, a tapered first sleeve portion 2311 extending from the collar, and a second sleeve portion 2312 extending from the first sleeve portion. In a housed configuration (not shown), the inner catheter 2304, framework 2306, control members 2308, collar 2310 and sleeve portions 2311, 2312 are held within the outer catheter 2301 and advanced to the location of interest within the artery 2320. In a deployed configuration, the inner catheter 2304 is advanced out of the distal end of the outer catheter 2301 and the control members 2308 are operated from the proximal end of the apparatus to deploy the framework 2306, collar 2310 and sleeves 2311, 2312 out of the outer catheter 2301 and over the inner catheter 2304. The collar 2310 expands the proximal end of the tapered first sleeve 2311 adjacent the arterial wall 2320. During forward blood flow 2322a which occurs when a relatively higher pressure condition is located upstream of the valve than downstream of the valve, the blood flows between the inner catheter 2304 and the sleeves 2311, 2312, similar to air flowing through a windsock. However, when the fluid pressure condition changes, with higher pressure downstream than upstream, at least the second sleeve 2312 is structured to collapse in response to prevent reverse flow 2322b of embolizing agent 2324 through the sleeves 2311, 3212. Agent 2324 contacts the exterior of the sleeves 2311, 2312 but cannot pass through.

Figure 34:
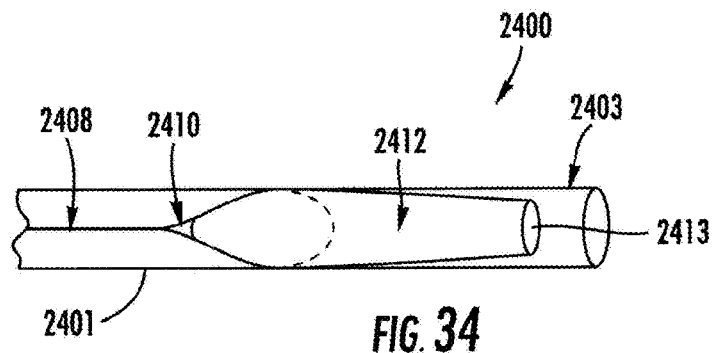
FIGS. 34-36 are schematic views of another apparatus for deployment of a valve, with FIG. 34 showing the valve in a housed configuration, FIG. 35 showing the valve deployed, and FIG. 36 showing the valve in use.
Figure 35:
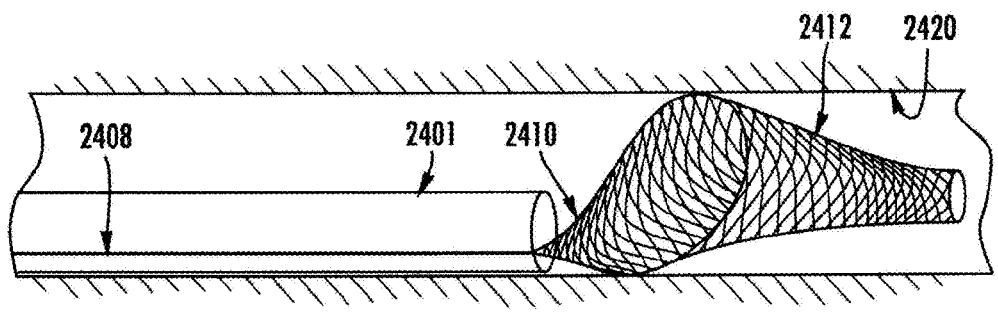
Figure 36:
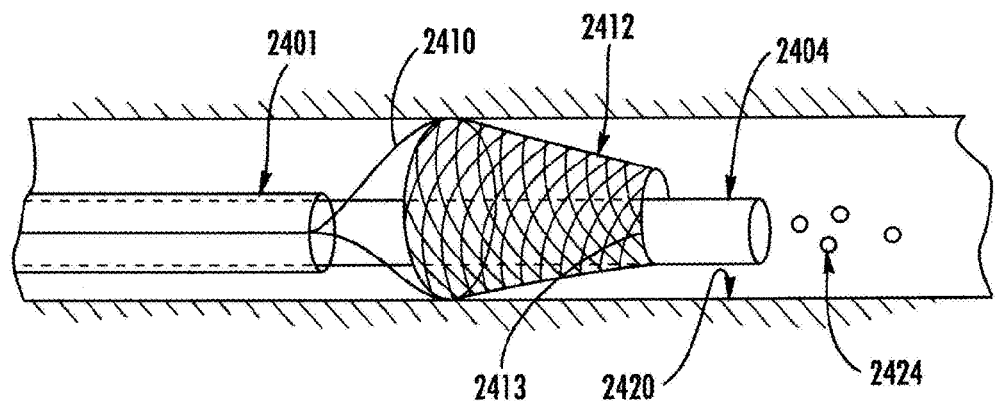

Turning now to FIGS. 34 through 36, another embodiment of a delivery device 2400 is shown. The delivery device 2400 includes a control member 2408 with a self-expanding shape memory loop (or collar) 2410 at its distal end. A valve 2412 extends from the loop 2410. The valve 2412 has an open distal end 2413. The control member 2408 is operated to advance the valve 2412 to the distal end 2403 of an outer catheter 2401 which is advanced to the arterial location of interest. Referring to FIG. 35, the control member 2408 is then operated to advance the loop and valve out of the distal end 2403 of the outer catheter 2401, with the loop automatically expanding and causing the proximal end of the valve 2412 to be positioned against or adjacent the arterial wall 2420. Then, as shown in FIG. 36, an inner catheter 2404 is advanced through the outer catheter 2401 and completely through the open distal end 2413 of the filter valve 2412. Embolizing agent 2424 is infused through the inner catheter 2404. Blood may flow in the forward direction between the inner catheter 2404 and filter valve 2412. During retrograde blood flow, such as when the pressure is increased through the inner catheter 2404, the loop 2410 retains its diameter against the arterial wall 2420, but the distal and central portions of the filter valve 2412 dynamically collapses against the inner catheter 2404 in response to the changing pressure preventing reverse flow of embolizing agent 2424 past the valve.

Figure 37:
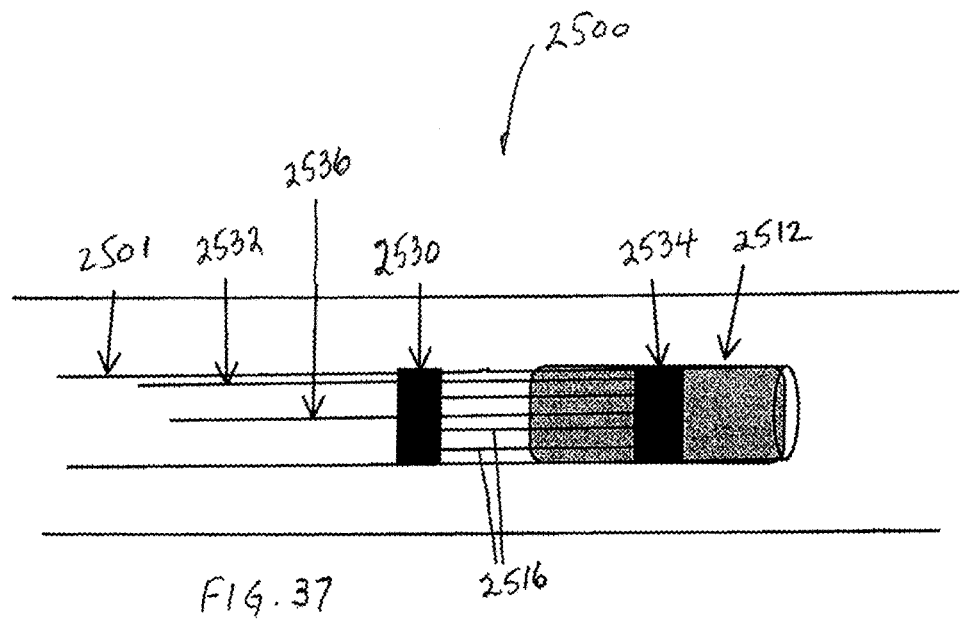
FIGS. 37-40 are schematic views of another embodiment of an apparatus for deployment of a valve, with FIG. 37 showing a initial closed configuration, FIGS. 38 and 39 illustrating deployed configurations, and FIG. 40 illustrated a re-assumed closed configuration.
Figure 38:
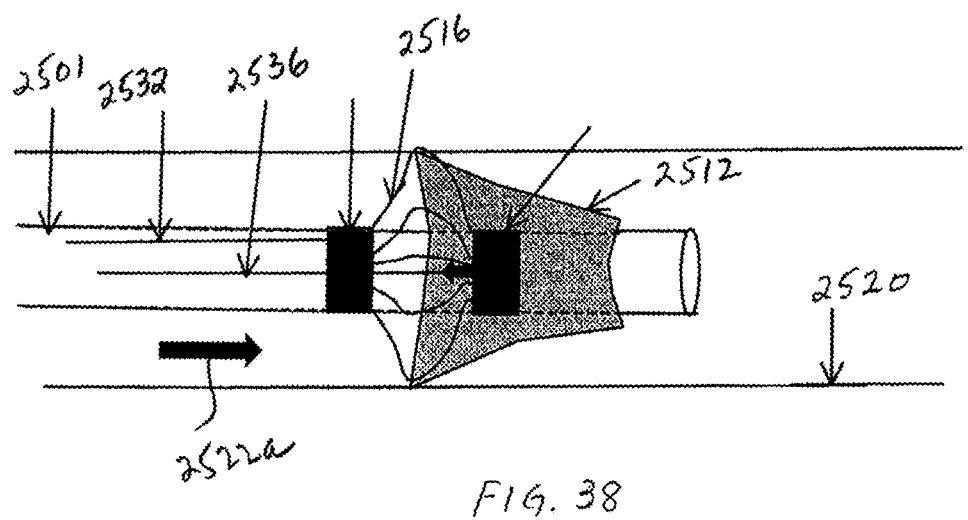
Figure 39:
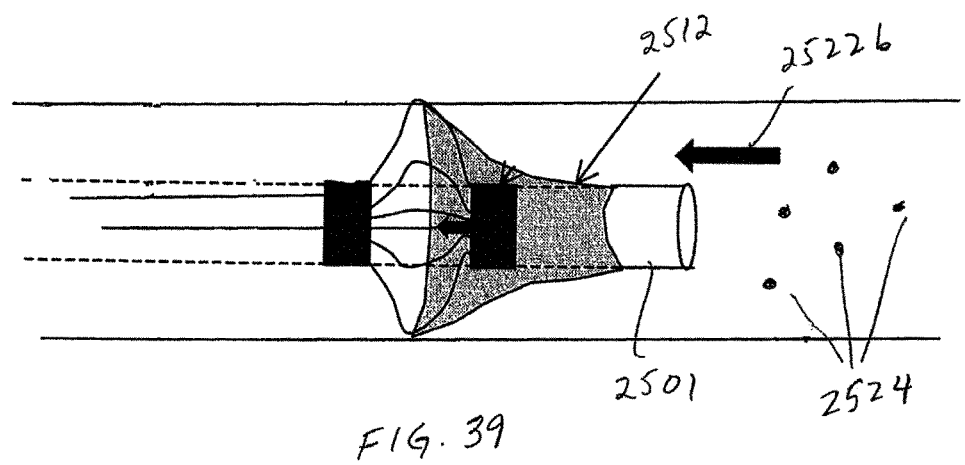
Figure 40:
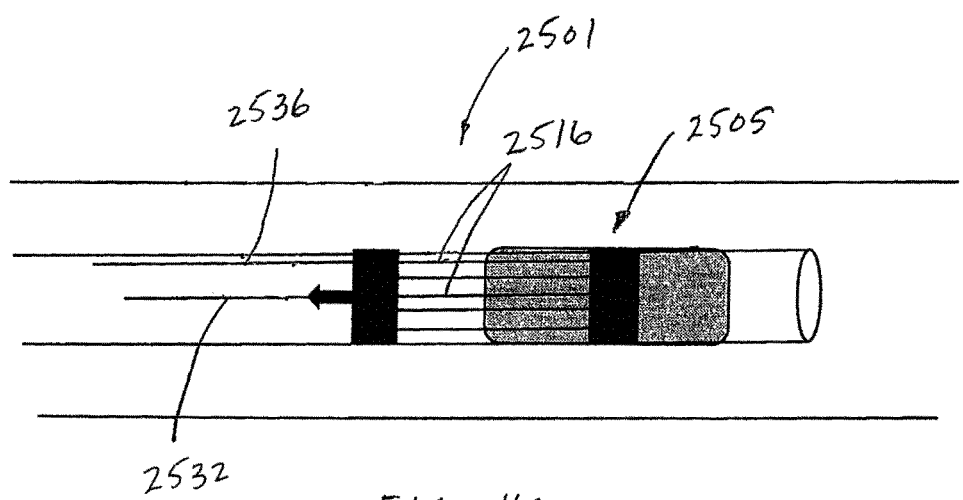

Referring now to FIG. 37 another embodiment of a delivery device 2500 is shown. The delivery device 2500 includes a catheter 2501, a first collar 2530 about the catheter 2501 and coupled to the catheter or a first control member 2532, a second collar 2534 displaced from the first collar 2530 and located about the catheter and coupled to a second control member 2536, a plurality of struts 2516 extending between the first and second collars 2530, 2534, and a valve sleeve 2512 extending over at least a portion of the struts 2516 and preferably the second collar 2534. Referring to FIG. 38, in operation, when the second control member 2536 is retracted relative to the catheter 2501 and/or first control member 2532 (i.e., whichever to which the first collar 2530 is coupled), the struts 2516 are caused to bow outwards thereby moving the proximal end of the valve sleeve 2512 against the arterial wall 2520. Embolizing agent 2524 may be injected through the catheter 2512. Forwardly advancing blood 2522a may flow between the valve sleeve 2512 and the catheter 2501. Referring to FIG. 39, when there is a rapid change in pressure against on the valve sleeve 2512, with higher pressure located on the downstream side, the valve sleeve 2512 dynamically reacts collapsing against the catheter 2501 to prevent retrograde flow of embolizing agent 2524 in the upstream direction 2522b. The delivery device 2500 may be collapsed for withdrawal by moving the first control member 2532 proximally relative to the second control member 2536 to straighten the struts 2516 and thereby reduce the diameter of the valve sleeve 2512 (FIG. 40).

Figure 41:
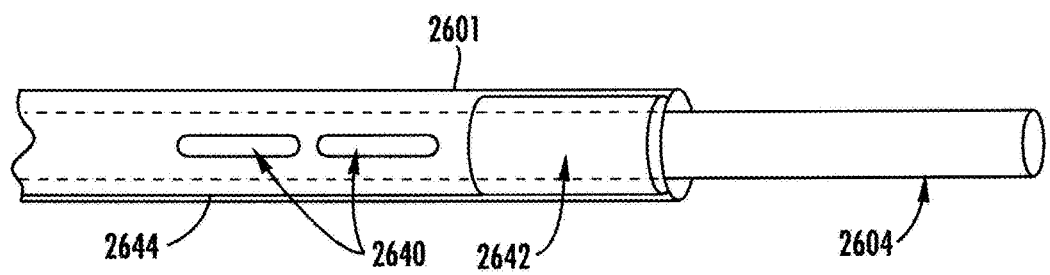
FIGS. 41-43 illustrate several flush valves usable in conjunction with any of the other embodiments of the invention.
Figure 42:
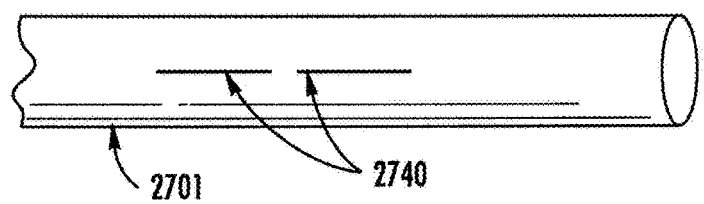
Figure 43:
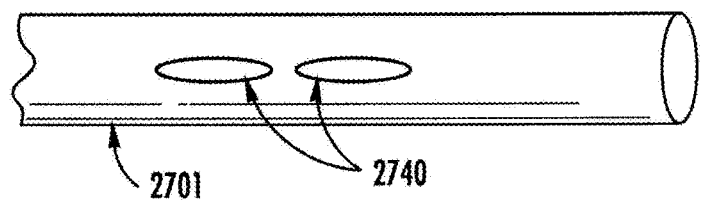

It is appreciated that it in any of the embodiments described above it may be desirable to controllably flush the outer catheter through a route that exits behind the valve. Such flush may include a contrast agent, saline, etc. Turning now to FIG. 41, one embodiment of a flush valve includes one or more open slits 2640 in the outer catheter 2601. A side stop 2642 is provided in the annular space between the outer and inner catheters 2601, 2604. Alternatively, the stop 2642 may be provided against an outer catheter 2601 in which no inner catheter is provided. The side stop 2642 is coupled at the distal end of a control member 2644. In a closed state, the proximal end of the control member 2644 is manipulated to position the side stop 2642 in obstruction of the open slits 2640 to prevent fluid passage therethrough. To permit flush, the proximal end of the control member 2644 is manipulated to position the side stop 2642 either proximal or distal (shown) relative to the open slits 2640 so that fluid may be flushed therethrough. Turning now to FIG. 42, another embodiment of a flush system is shown incorporating slit valves 2740 in the outer catheter 2701. Such slit valves 2740 are normally in a closed configuration. However, upon application of a flush under pressure, the slit valves 2740 are opened and the flush is permitted to escape the catheter (FIG. 43).

Figure 44:
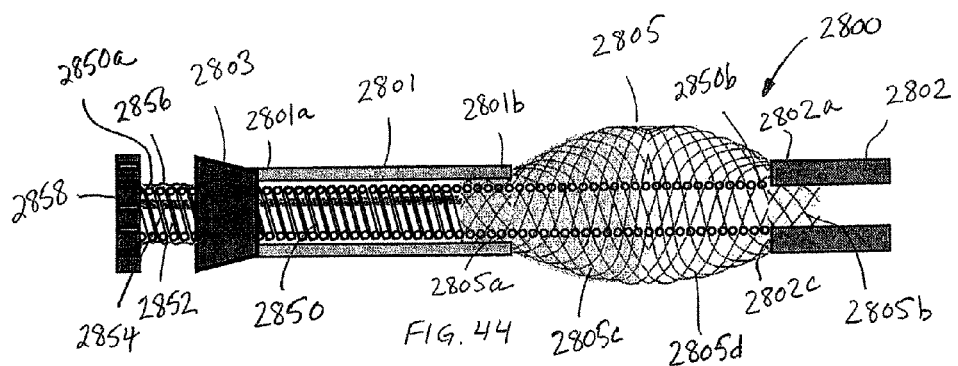
FIGS. 44-47 are schematic illustrations of another embodiment of an apparatus for deployment of valve.

Turning now to FIG. 44, another embodiment of a valve deployment apparatus 2800 is shown. The apparatus 2800 includes two longitudinally displaced microcatheters 2801, 2802 and a dynamic valve 2805 located therebetween. More particularly, the more proximal first microcatheter 2801 is a "hi-flo" microcatheter preferably having an inner diameter of 0.69 mm and an outer diameter of 0.97 mm and includes a proximal luer 2803 or other suitable connector at its proximal end 2801a and has a distal end 2801b. The distal second microcatheter 2802 preferably has a proximal end 2802a with a proximal face 2802c, a smaller inner diameter of 0.53 mm, and the same 0.97 mm outer diameter as the first microcatheter. The valve 2805 preferably comprises a braid that is fused at its proximal end 2805a to the distal end 2801b of the first microcatheter 2801 and at its distal end 2805b to the proximal end 2802b of the second microcatheter 2802. The braid is naturally biased to radially self-expand from an undeployed state to a deployed state, wherein the valve in the undeployed state (described below) has a diameter approximately equal to the outer diameter of the first and second microcatheters, and into the deployed states has a diameter substantially greater. The braid includes a proximal portion 2805c that is polymer coated as described with respect to several valves described above, whereas a distal portion 2805d of the braid is uncoated and forms an open design permitting fluid to flow therethrough.

The apparatus 2800 further includes a thin-walled tubular elongate member 2850 preferably having an inner diameter of 0.53 mm and an outer diameter of 0.64 mm. The tubular member 2850 is most preferably in the form of a wire coil 2852 preferably with an axially extending peripheral wire 2854 or oversheath 2856 for longitudinal stability. The coil tubular member has a proximal end 2850a provided with a hub 2858 for locking relative to the luer connector 2803, such as a tuohy borst adapter and a distal end 2850b. When the coil tubular member 2850 is inserted into the luer connector 2803, through the first microcatheter 2801, and through the valve 2805, its distal end 2850b abuts the proximal face 2802c of the second microcatheter 2802. The coil tubular member 2850 is sized such that when fully advanced into the first microcatheter 2801, the proximal end 2802a of the second microcatheter 2802 is displaced from the distal end 2801b of the first microcatheter 2802 a sufficient distance to apply a tensile force on the valve to cause the valve to elongate and constrict in diameter to a significantly smaller non-deployed diameter suitable for advancement through the vessel. The apparatus 2800 may be presented in this configuration in an as manufactured and/or sterilized package.

Figure 45:
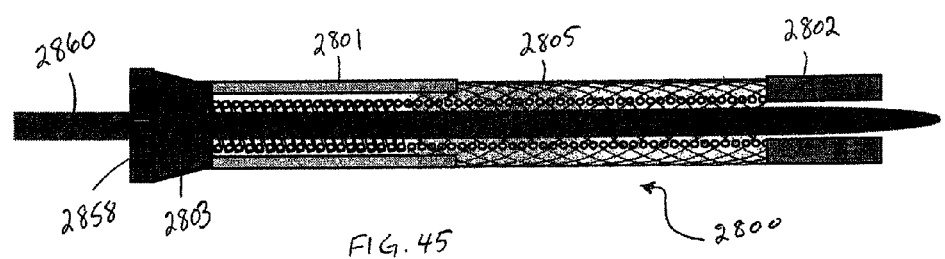

Referring to FIG. 45, a standard 0.356 mm guidewire 2860 is provided for use with the apparatus 2800. The guidewire 2860 is inserted through the hub 2858 and luer connector 2803 and through the first microcatheter 2801, the valve 2805 and the second microcatheter 2802. The guidewire 2860 is advanced to the site of the emboli and the apparatus 2800 is then tracked over the guidewire to the site.

Figure 46:
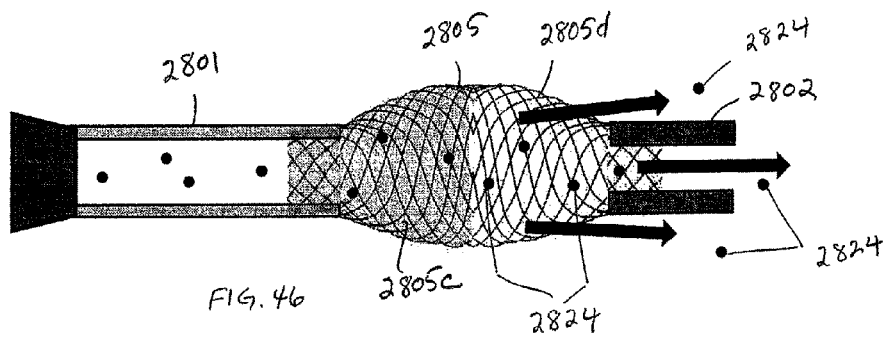

Referring to FIG. 46, the guidewire 2860 is shown withdrawn, and the coil tubular member 2850 is released from the luer connector 2803 and removed from the first microcatheter 2801, allowing the valve 2805 to expand to the arterial wall (not shown). Embolizing agent 2824 is then infused through the first microcatheter 2801 and exits through the uncoated distal portion 2805*d* of the valve and the second microcatheter 2802. Importantly, the valve 2805, even through coupled at its distal end to the second microcatheter, is a dynamic valve rapidly adjusting to pressure conditions resulting from changing blood pressure in systole and diastole and the pressure of infused embolic agent. Thus, during the forward flow of blood in systole; i.e., when fluid pressure is higher upstream of the valve than downstream of the valve, the coated proximal portion 2805*c* of the valve collapses to permit the blood to flow around the valve. Further, during e.g., retrograde blood flow upon infusion of embolic agent, the coated proximal portion of the valve opens against the arterial wall preventing passage of any of the embolizing agent.

Figure 47:
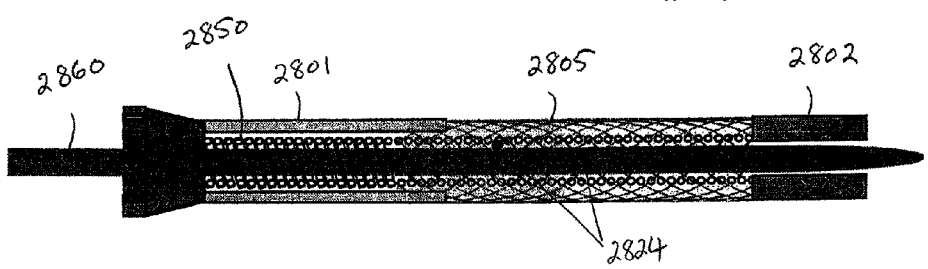

Turning to FIG. 47, after the procedure, the device comprising the microcatheters 2801, 2802 and valve 2805 may simply be withdrawn from the artery which will automatically collapse the valve. However, as an option, the coil tubular member 2805 may be reinserted to aid in collapse and the guidewire 2860 may also optionally be reinserted to facilitate reverse tracking out of the patient. Regardless of the method of removal, it is appreciated that any embolizing agent 2824 remaining in the valve upon collapse of the valve will remain trapped in the valve for retrieval as the braid angle will be reduced in size upon collapse to define openings too small for the embolizing agent to pass through.

Figure 48:
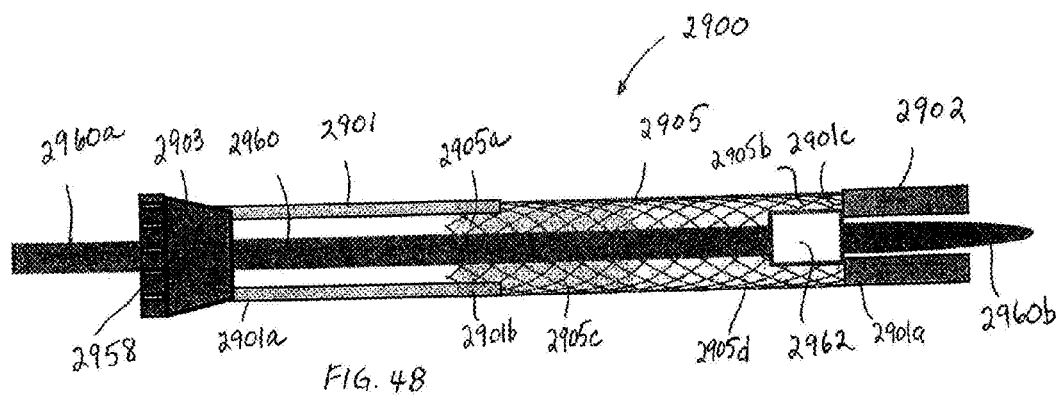
FIGS. 48-51 are schematic illustrations of another embodiment of an apparatus for deployment of valve.
Figure 49:
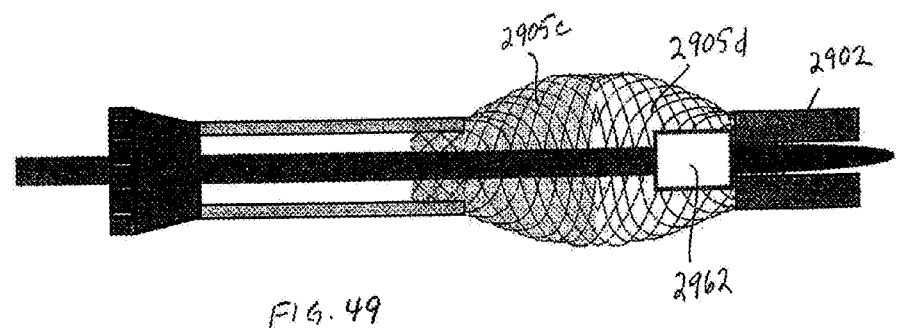

Turning now to FIGS. 48 and 49, another embodiment of a valve deployment apparatus 2900, substantially similar to the deployment apparatus 2800, is shown. The apparatus 2900 includes two longitudinally displaced microcatheters 2901, 2902 and a dynamic valve 2905 located therebetween. More particularly, the more proximal first microcatheter 2901 is a "hi-flo" microcatheter preferably having an inner diameter of 0.69 mm and an outer diameter of 0.97 mm and includes a connector 2903 at its proximal end 2901*a* and has a distal end 2901*b*. The distal second microcatheter 2902 preferably has a proximal end 2902*a* with a proximal face 2902*c*, a smaller inner diameter of 0.53 mm, and the same 0.97 mm outer diameter as the first microcatheter. The valve 2905 preferably comprises a braid that is fused at its proximal end 2905*a* to the distal end 2901*b* of the first microcatheter 2901 and at its distal end 2905*b* to the proximal end 2902*b* of the second microcatheter 2902. The braid includes a proximal portion 2905*c* that is polymer coated as described with respect to several valves described above, whereas a distal portion 2905*d* of the braid is uncoated and forms an open design permitting fluid to flow therethrough.

The apparatus 2900 further includes an elongate member such as a guidewire 2960. The guidewire 2960 is preferably a 0.45 mm diameter guidewire, but may be other dimensions, and includes a hub 2958 adjacent its proximal end 2960*a* and a preferably radiopaque marker band 2962 adjacent its distal end 2960*b*. The marker band 2962 is larger than the inner diameter of the second microcatheter and is thus adapted to abut against the proximal face 2902*c*. A fixed length is indicated, whether by actual length, indicia, or stops between the guide wire from the proximal 2901*a* end of the first microcatheter 2901 or the distal end of the marker band 2962. The guidewire is inserted through the first microcatheter such fixed length so that the marker band is abutted against proximal face of the second microcatheter; this results in the valve entering the collapsed configuration. The apparatus with guidewire is then advanced to the target. Once at the target the guidewire is removed from the apparatus.

Figure 50:
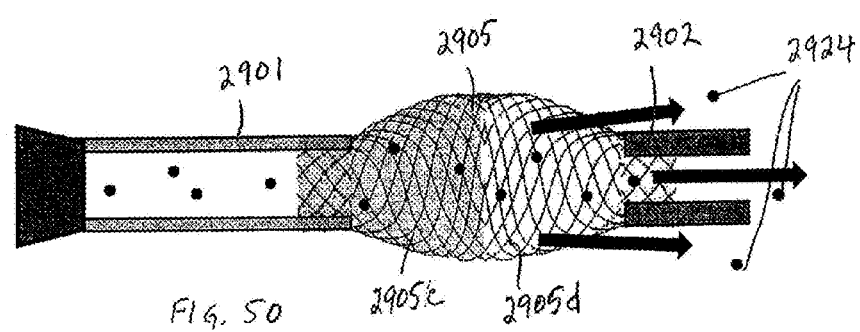

Referring to FIG. 50, the apparatus in use is substantially similar to that described above with respect to FIG. 46. The valve 2905 expands to the arterial wall (not shown). Embolizing agent 2924 is then infused under pressure through the first microcatheter 2901 and exits through the uncoated distal portion 2905*d* of the valve and the second microcatheter 2902. Importantly, the valve 2905, even through coupled at its distal end to the second microcatheter, is a dynamic valve rapidly adjusting to pressure conditions resulting from changing blood pressure in systole and diastole and the pressure of infused embolic agent. Thus, during the forward flow of blood in systole; i.e., when fluid pressure is higher upstream of the valve than downstream of the valve, the coated proximal portion 2905*c* of the valve collapses to permit the blood to flow around the valve. Further, during e.g., retrograde blood flow upon infusion of embolic agent, the coated proximal portion of the valve opens against the arterial wall preventing passage of any of the embolizing agent.

Figure 51:
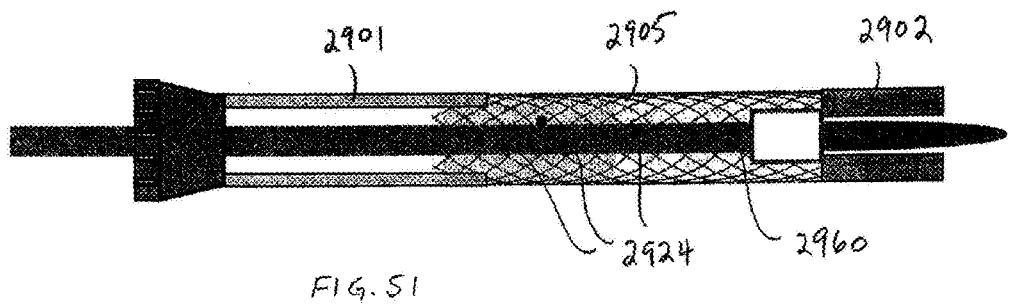

Turning to FIG. 51, after the procedure, the device comprising the microcatheters 2901, 2902 and valve 2905 can be withdrawn by simply retracting it from the artery which will cause collapse of the valve. However, optionally, the guidewire 2960 may be reinserted to collapse the valve 2905. It is appreciated that any embolizing agent 2924 remaining in the valve upon collapse of the valve will remain trapped in the valve for retrieval as the braid angle will be reduced in size upon collapse to define openings too small for the embolizing agent to pass through.

In any of the embodiments described herein, the components of the valve may be coated to reduce friction in deployment and retraction. The components may also be coated to reduce thrombus formation along the valve or to be compatible with therapeutics, biologics, or embolics. The components may be coated to increase binding of embolization agents so that they are removed from the vessel during retraction.

According to one aspect of the invention, the catheter body and mesh may be separately labeled for easy visualization under fluoroscopy. The catheter body can be labeled by use of any means known in the art; for example, compounding a radio-opaque material into the catheter tubing. The radio-opaque material can be barium sulfate, bismuth subcarbonate or other material. Alternatively or additionally, radio-opaque rings can be placed or crimped onto the catheter, where the rings are made of platinum, platinum iridium, gold, tantalum, and the like. The valve may be labeled by crimping a small radio-opaque element such as a ring on one or a plurality of filaments. Alternatively or additionally, radio-opaque medium can be compounded into the materials of the braid and the filter. Or, as previously described, one or more of the filaments may be chosen to be made of a radio-opaque material such as platinum iridium.

In certain embodiments, the valve is attached to a catheter which may be a single lumen or a multi-lumen catheter. Preferably, the catheter has at least one lumen used to deliver the embolization agents. According to other embodiments, however, the catheter may provided with a lumen which either serves to store the valve before deployment or through which the valve can be delivered. Where control members are utilized to control deployment of the valve, one or more additional lumen may be provided, if desired, to contain the control wires for deployment and retraction. Alternatively, the catheter about which the control members extends may include longitudinal open channels through which the control wires may extend. An additional lumen may also be used to administer fluids, e.g., for flushing the artery after the administration of embolization agents, or for controlling a balloon which could be used in conjunction with the valve.

The above apparatus and methods have been primarily directed to a system which permits proximal and distal flow of biological fluid (e.g., blood) within a body vessel, and which prevents reflux of an infusate past the valve in a proximal direction. It is appreciated that the valve may also be optimized to reduce blood flow in the distal direction. The radial force of the valve can be tuned by adjusting the braid angle. Tuning the radial force allows the blood flow to be reduced by up to more than 50 percent. By way of example, providing a braid angle greater than 130° will significantly reduce blood flow past the valve in the distal direction, with a braid angle of approximately 150° slowing the blood flow by 50 to 60 percent. Other braid angles can provide different reductions in distal blood flow. The reduced distal blood flow can be used in place of a 'wedge' technique, in which distal blood flow is reduced for treatment of brain and spinal arteriovenous malformations. Once the blood flow is slowed by the valve, a glue such as a cyanoacrylic can be applied at the target site.

There have been described and illustrated herein multiple embodiments of devices and methods for reducing or preventing reflux of embolization agents in a vessel. While particular embodiments of the invention have been described, it is not intended that the invention be limited thereto, as it is intended that the invention be as broad in scope as the art will allow and that the specification be read likewise. Thus while particular deployment means for the protection valve have been described, such as a catheter, a sleeve and control element, a fabric sleeve with a control thread, etc., it will be appreciated that other deployment mechanisms such as balloons, absorbable sleeves, or combinations of elements could be utilized. Likewise, while various materials have been listed for the valve filaments, the valve filter, the catheter, and the deployment means, it will be appreciated that other materials can be utilized for each of them. Also, while the invention has been described with respect to particular arteries of humans, it will be appreciated that the invention can have application to any blood vessel and other vessels, including ducts, of humans and animals. In particular, the apparatus can also be used in treatments of tumors, such as liver, renal or pancreatic carcinomas. Further, the embodiments have been described with respect to their distal ends because their proximal ends can take any of various forms, including forms well known in the art. By way of example only, the proximal end can include two handles with one handle connected to the inner (delivery) catheter, and another handle connected to an outer catheter or sleeve or actuation wire or string. Movement of one handle in a first direction relative to the other handle can be used to deploy the valve, and where applicable, movement of that handle in an opposite second direction can be used to recapture the valve. Depending upon the handle arrangement, valve deployment can occur when the handles are moved away from each other or towards each other. As is well known, the handles can be arranged to provide for linear movement relative to each other or rotational movement. If desired, the proximal end of the inner catheter can be provided with hash-marks or other indications at intervals along the catheter so that movement of the handles relative to each other can be visually calibrated and give an indication of the extent to which the valve is opened. It will therefore be appreciated by those skilled in the art that yet other modifications could be made to the provided invention without deviating from its spirit and scope as claimed.

We claim:

1. An endovascular valve device for temporary use in a vessel during an intravascular procedure, comprising:
   a) a first catheter having a distal end, a lumen defining an inner diameter and terminating at a distal orifice, and an outer diameter; and
   b) a valve fixed to said distal end of said first catheter, said distal orifice opening into an interior of said valve, said valve having,
      i) a plurality of elongate first filaments in a braid, said first filaments having a proximal end, a distal end, and a length extending therebetween,
      said proximal ends of said first filaments secured relative to each other such that a central opening is provided between said secured proximal ends, said first filaments along said lengths distal of said proximal ends movable relative to each other,
      said first filaments fully collapsible relative to each other into an undeployed state, and expandable from said undeployed state into a radially-expanded deployed state by a spring bias of said first filaments, and
      ii) a polymeric filter coated onto said braid,
      wherein once said valve is in said deployed state in the vessel, said valve is dynamically movable between an expanded valve-open configuration and a collapsed valve-closed configuration depending on a local fluid pressure about said valve such that,
      when the fluid pressure is higher on a proximal side of said valve, the higher fluid pressure on said proximal side of said valve causes said valve to assume said valve-closed configuration in which said distal end of said valve assumes a first maximum diameter smaller than the diameter of the vessel such that fluid flow about the said valve and said filter is permitted, and
      when said fluid pressure is higher on a distal side of said valve, the higher fluid pressure on said distal side of said valve causes said valve to assume said valve-open configuration in which said distal end of said valve assumes a second maximum diameter relatively larger than said first maximum diameter and in which said valve is adapted to contact the vessel wall.

2. An endovascular valve device according to claim 1, wherein:
   said filter defining a pore size not exceeding 500 μm.

3. An endovascular valve device according to claim 1, wherein:
   said valve automatically expands when one of (i) a biological fluid flows against said valve in a distal to proximal direction, (ii) the biological fluid is at a static flow condition, or (iii) there is a fluid pressure on the proximal side of said valve which is different than a fluid pressure on the distal side of said valve, a difference in fluid pressure between said proximal and distal sides of said valve creating a net fluid pressure on said proximal side of said valve, and said net fluid pressure is less than a radial force of expansion of said valve.

4. An endovascular valve device according to claim 1, wherein:
   said valve automatically collapses into said valve-closed configuration during systole and automatically expands into said valve-open configuration during diastole.

5. An endovascular valve device according to claim 1, wherein:
said polymeric filter comprises polymeric second filaments electrostatically deposited or spun onto said braided first filaments.

6. An endovascular valve device according to claim 1, wherein:
said first filaments are comprised of a material chosen from polyethylene terephthalate (PET), polyethylene-napthalate (PEN), liquid crystal polymer, stainless steel, Nitinol, fluorinated polymers, nylon, polyamide, platinum or platinum-iridium.

7. An endovascular valve device according to claim 1, wherein:
said first filaments form a substantially frustoconical shape when said valve is in said deployed state.

8. An endovascular valve device according to claim 1, wherein:
said valve in said undeployed state has a diameter approximately equal to said outer diameter of said first catheter, and in said deployed state has a diameter substantially larger than said outer diameter of said first catheter.

9. An endovascular valve device according to claim 1, further comprising:
a second catheter extending over the first catheter, wherein in said undeployed state said second catheter extends over said valve and in said deployed state said valve extends distal of said second catheter.

10. An endovascular valve device for temporary use in a vessel during an intravascular procedure, the device comprising:
a) an elongated first catheter having a proximal end and a distal end, a lumen defining an inner diameter and terminating at a distal orifice, and an outer diameter; and
b) a substantially frustoconical valve longitudinally fixed at said distal end of said first catheter such that said distal orifice opens into an interior of said valve, said valve having a housed state with a first smaller diameter and a radially-expanded deployed state with a second larger diameter, said second larger diameter being substantially larger than said outer diameter and capable of extending across a vessel through which said device is used, said valve comprising,
i) a plurality of elongate first filaments in a braid, the braid expandable from an undeployed state into a radially-expanded deployed state by a spring bias of said first filaments, and
ii) a filter comprising a polymeric coating on said braid, said filter defining a pore size not exceeding 500 μm, wherein once said valve is in said deployed state in the vessel, said valve is dynamically movable between an expanded valve-open configuration and a collapsed valve-closed configuration depending on a local fluid pressure about said valve,
when the fluid pressure is higher on a proximal side of said valve, the higher fluid pressure on said proximal side of said valve causes said valve to assume said valve-closed configuration in which said distal end of said valve assumes a first maximum diameter smaller than the diameter of the vessel such that fluid flow about said valve and said filter is permitted, and
when said fluid pressure is higher on a distal side of said valve, the higher fluid pressure on said distal side of said valve causes said valve to assume said valve-open configuration in which said distal end of said valve assumes a second maximum diameter relatively larger than said first maximum diameter and in which said valve is adapted to contact the vessel wall.

11. An endovascular valve device according to claim 10, wherein:
said valve has an opening at a proximal end of said braid, and said opening is in fluid communication with said lumen of said delivery catheter.

12. An endovascular valve device according to claim 10, wherein:
each of said first filaments having a diameter of 0.025 mm to 0.127 mm.

13. An endovascular valve device according to claim 10, wherein:
said polymeric coating comprises polymeric second filaments electrostatically deposited or spun onto said braided first filaments.

14. An endovascular valve device according to claim 10, further comprising:
a control element, said control element and said first catheter displaceable relative to each other for deploying said valve from said housed state to said deployed state.

15. An endovascular valve device according to claim 14, wherein:
said control element is a second catheter, said first catheter extending within said second catheter.

16. An endovascular valve device for temporary use in a vessel during an intravascular procedure, the device comprising:
a) an elongated first catheter having a proximal end and a distal end, a lumen defining an inner diameter and a distal orifice, and an outer diameter; and
b) a valve coupled at said distal end of said first catheter, said valve having a substantially frustoconical portion with a proximal portion and a distal portion, said proximal portion of said frustoconical portion coupled to said first catheter such that said distal orifice opens into an interior of said valve, said valve comprising,
i) a plurality of elongate first filaments in a braid, the braid expandable from an undeployed state into a radially-expanded deployed state by a spring bias of said first filaments, and
ii) a filter comprising a polymeric coating on said braid, said filter defining a pore size not exceeding 500 μm, wherein once said valve is in said deployed state in the vessel, said valve is dynamically movable between an expanded valve-open configuration and a collapsed valve-closed configuration depending on a local fluid pressure about said valve, wherein,
when the fluid pressure is higher on a proximal side of said valve, the higher fluid pressure on said proximal side of said valve causes said valve to assume said valve-closed configuration in which said distal end of said valve assumes a first maximum diameter, and
when said fluid pressure is higher on a distal side of said valve, the higher fluid pressure on said distal side of said valve causes said valve to assume said valve-open configuration in which said distal end of said valve assumes a second maximum diameter larger than the first maximum diameter.

17. An endovascular valve device according to claim 16, wherein:
said proximal end of said valve is longitudinally fixed coaxially about said first catheter.

18. An endovascular valve device according to claim 16, further comprising:
   a second catheter extending over the first catheter, wherein in said undeployed state said second catheter extends over said valve and in said deployed state said valve extends distal of said second catheter.

19. An endovascular valve device according to claim 16, wherein:
   said polymeric filter comprises polymeric second filaments electrostatically deposited or spun onto said braided first filaments.

* * * * *